US007999118B2

(12) United States Patent
Elnagar et al.

(10) Patent No.: US 7,999,118 B2
(45) Date of Patent: *Aug. 16, 2011

(54) PROCESS FOR PRODUCING N-HALOGENATED HYDANTOINS

(75) Inventors: Hassan Y. Elnagar, Baton Rouge, LA (US); Bruce C. Peters, Baton Rouge, LA (US); Edgar E. Spielman, Jr., Baton Rouge, LA (US); Dustin H. Thomas, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 1612 days.

This patent is subject to a terminal disclaimer.

(21) Appl. No.: 11/251,640

(22) Filed: Oct. 17, 2005

(65) Prior Publication Data

US 2006/0036099 A1 Feb. 16, 2006

Related U.S. Application Data

(63) Continuation-in-part of application No. 10/919,097, filed on Aug. 16, 2004, now abandoned, which is a continuation-in-part of application No. 09/484,844, filed on Jan. 18, 2000, now Pat. No. 6,809,205.

(51) Int. Cl.
*C07D 233/74* (2006.01)
*C07D 233/82* (2006.01)

(52) U.S. Cl. .................................................. 548/320.5

(58) Field of Classification Search ................. 548/320.5
See application file for complete search history.

(56) References Cited

U.S. PATENT DOCUMENTS

| | | | |
|---|---|---|---|
| 2,130,805 A | 9/1938 | Levine |
| 2,392,505 A | 1/1946 | Rogers |
| 2,398,598 A | 4/1946 | Rogers |
| 2,779,764 A | 1/1956 | Paterson |
| 2,795,556 A | 6/1957 | Quinn |
| 2,868,787 A | 1/1959 | Paterson |
| 2,920,997 A | 1/1960 | Wolf et al. |
| 2,969,360 A | 1/1961 | Westfall |
| 2,971,959 A | 2/1961 | Waugh et al. |
| 2,971,960 A | 2/1961 | Waugh et al. |
| 3,121,715 A | 2/1964 | Waugh et al. |
| 3,147,259 A | 9/1964 | Paterson |
| 3,345,371 A | 10/1967 | Paterson |
| 3,626,972 A | 12/1971 | Lorenzen |
| 4,078,099 A | 3/1978 | Mazzola |
| 4,126,717 A | 11/1978 | Mazzola |
| 4,136,052 A | 1/1979 | Mazzola |
| 4,199,001 A | 4/1980 | Kratz |
| 4,242,216 A | 12/1980 | Daugherty et al. |
| 4,270,565 A | 6/1981 | King, Sr. |
| 4,293,425 A | 10/1981 | Price |
| 4,327,151 A | 4/1982 | Mazzola |
| 4,331,174 A | 5/1982 | King, Sr. |
| 4,382,799 A | 5/1983 | Davis et al. |
| 4,427,692 A | 1/1984 | Girard |
| 4,465,839 A | 8/1984 | Schulte et al. |
| 4,532,330 A | 7/1985 | Cole |
| 4,537,697 A | 8/1985 | Girard |
| 4,560,766 A | 12/1985 | Girard et al. |
| 4,571,333 A | 2/1986 | Hsiao et al. |
| 4,597,941 A | 7/1986 | Bottom et al. |
| 4,621,096 A | 11/1986 | Cole |
| 4,654,424 A | 3/1987 | Girard et al. |
| 4,662,387 A | 5/1987 | King, Sr. |
| 4,677,130 A | 6/1987 | Puzig |
| 4,698,165 A | 10/1987 | Theyson |
| 4,713,079 A | 12/1987 | Chun et al. |
| 4,728,453 A | 3/1988 | Choy |
| 4,745,189 A | 5/1988 | Lee et al. |
| 4,780,197 A | 10/1988 | Schuman |
| 4,803,079 A | 2/1989 | Hsiao et al. |
| 4,867,895 A | 9/1989 | Choy |
| 4,919,841 A | 4/1990 | Kamel et al. |
| 4,925,866 A | 5/1990 | Smith |
| 5,076,315 A | 12/1991 | King |

(Continued)

FOREIGN PATENT DOCUMENTS

| | | |
|---|---|---|
| CA | 1230825 | 12/1987 |
| CA | 2042430 | 11/1991 |
| CA | 2163596 | 9/1996 |
| CN | 1432279 | 7/2003 |
| EP | 0177645 A1 | 4/1986 |
| EP | 0206725 | 12/1986 |
| EP | 0228593 | 7/1987 |
| EP | 0581826 | 2/1994 |
| GB | 1054243 | 1/1967 |
| GB | 1139188 | 1/1969 |

(Continued)

OTHER PUBLICATIONS

Corral et al., "Substitution in the Hydantoin Ring. III. Halogenation", J. Org. Chem., 1963, vol. 28, pp. 1100-1104.

(Continued)

*Primary Examiner* — Laura L. Stockton
(74) *Attorney, Agent, or Firm* — Marcy M. Hoefling

(57) ABSTRACT

This invention provides a process for the N-halogenation of at least one 5-hydrocarbyl hydantoin and/or at least one 5,5-dihydrocarbyl hydantoin. The process comprises concurrently feeding into a reaction zone (i) water, inorganic base, and 5,5-dimethylhydantoin, these being fed separately and/or in any combination(s), (ii) a separate feed of a brominating agent, and (iii) a separate feed of a chlorinating agent, in proportions such that during all or substantially all of the time the concurrent feeding is occurring halogenation of the 5-hydrocarbyl hydantoin and/or 5,5-dihydrocarbyl hydantoin occurs and resultant halogenated product precipitates in the liquid phase of an aqueous reaction mixture, and in which the pH of the liquid phase is continuously or substantially continuously maintained in the range of about 2.0 to about 8.0 during all or substantially all of the time the concurrent feeding is occurring. Also provided by this invention is a composition of matter which is a halogenated 5-hydrocarbyl hydantoin or a halogenated 5,5-dihydrocarbyl hydantoin, which is a mixture of the 1,3-dibromo-, 1,3-dichloro-, and/or N,N'-bromochloro-species of the halogenated hydantoin.

47 Claims, No Drawings

U.S. PATENT DOCUMENTS

| | | | |
|---|---|---|---|
| 5,137,563 | A | 8/1992 | Valkanas |
| 5,218,983 | A | 6/1993 | King |
| 5,338,461 | A | 8/1994 | Jones |
| 5,339,889 | A | 8/1994 | Bigham |
| 5,384,102 | A | 1/1995 | Ferguson et al. |
| 5,403,813 | A | 4/1995 | Lichti et al. |
| 5,409,711 | A | 4/1995 | Mapelli et al. |
| 5,422,126 | A | 6/1995 | Howarth et al. |
| 5,476,116 | A | 12/1995 | Price et al. |
| 5,565,109 | A | 10/1996 | Sweeny |
| 5,565,576 | A | 10/1996 | Hall et al. |
| 5,578,559 | A | 11/1996 | Dolan et al. |
| 5,591,692 | A | 1/1997 | Jones et al. |
| 5,603,941 | A | 2/1997 | Farina et al. |
| 5,610,126 | A | 3/1997 | Barford et al. |
| 5,614,528 | A | 3/1997 | Jones et al. |
| 5,670,451 | A | 9/1997 | Jones et al. |
| 5,750,061 | A | 5/1998 | Farina et al. |
| 5,753,602 | A | 5/1998 | Hung et al. |
| 5,756,440 | A | 5/1998 | Watanabe et al. |
| 5,763,376 | A | 6/1998 | Ward et al. |
| 5,780,641 | A | 7/1998 | Yerushalmi et al. |
| 5,859,060 | A | 1/1999 | Platt |
| 5,942,153 | A | 8/1999 | Heydel |
| 5,958,853 | A | 9/1999 | Watanabe |
| 5,972,864 | A | 10/1999 | Counts |
| 5,981,461 | A | 11/1999 | Counts et al. |
| 5,984,994 | A | 11/1999 | Hudson |
| 6,284,144 | B1 | 9/2001 | Itzhak |
| 2006/0036099 | A1 | 2/2006 | Elnagar et al. |

FOREIGN PATENT DOCUMENTS

| | | |
|---|---|---|
| GB | 1600289 | 10/1981 |
| GB | 2273106 | 6/1994 |
| WO | WO-8910696 A1 | 11/1989 |
| WO | 9633964 | 10/1996 |
| WO | WO-9630491 A1 | 10/1996 |
| WO | WO-9715652 A1 | 5/1997 |
| WO | WO-9720546 A1 | 6/1997 |
| WO | WO-9720909 A1 | 6/1997 |
| WO | WO-97/43264 | 11/1997 |
| WO | WO-9743392 | 11/1997 |
| WO | WO-0034186 A1 | 6/2000 |
| WO | WO-03001931 A1 | 1/2003 |

OTHER PUBLICATIONS

Jolles, "General Methods of Bromination", Bromine and its Compounds, 1966, Ernest Benn, London, p. 365.
Markish et al., "New Aspects on the Preparation of 1,3-Dibromo-5,5-Dimethylhydantoin", Ind. Eng. Chem. Res. 1995, vol. 34, pp. 2125-2127.
Orazi et al., "Halogenacion con 3-Bromo-5,5-Dimetil-Hidantoina", Anales Assoc. Quim. Argentina, 1949, vol. 37, pp. 192-196. (Not translated).
Orazi et al., "Halogenacion Con 1-3-Dibromo-5,5-Dimetil-Hidantoina", Anales Assoc. Quim. Argentina, 1950, vol. 38, pp. 5-11. (Not translated).
HCAPLUS Abstract of JP 07171576 A2 issued 1995.
HCAPLUS Abstract of JP 07277912 A2 issued 1995.
HCAPLUS Abstract of JP 08027119 A2 issued 1996.
HCAPLUS Abstract of JP 08239699 A2 issued 1996.
HCAPLUS Abstract of JP 09087684 A2 issued 1997.
HCAPLUS Abstract of JP 09227317 A2 issued 1997.
Al Zahrani, S.M., "Utilization of Polyethylene and Paraffin Waxes as Controlled Deliveery Systems for Different Fertilizers", Ind. Eng. Chem. Res., 2000, vol. 39, pp. 369-371.
Author unknown, "Big Brother Brominator—Brominators", Bulky Systems Website, <http://www.bulkysystemsinc.com/brominator.html>, (Visited Aug. 10, 2001). 1 page.
Author unknown, "Bio Lab Brominator", Conely Company Website, <http://www.conelyco.com/Pool-Spa/parts/biobrom.htm> (Visited Aug. 10, 2001), 2 pages.
Beihoffer, Jon et al., "Identification and Determination of the Isomeric Bromo-and/or Chloro-Substituted 1,3-Dihalo-5,5-Dimethylhydantoins Used in Disinfectants and Mollusicicides", Journal of AOAC International, vol. 79, No. 4, 1996, pp. 823-828.
Chowhan et al., "Hardness Increase Induced by Partial Moisture Loss in Compressed Tablets and Its Effect on in Vitro Dissolution", J. Pharm. Sciences, Oct. 1978, vol. 67, No. 10, pp. 1385-1389.
Discount Pool & Spa Supplies, Automatic Chlorinators and Chemical Feeders Website, <http://www.discountpoolsupplies.com/Chemfeeders/> Visited Aug. 10, 2001, 3 pages.
Hayward America's #1 Pool Water Systems Product Catalog, "Automatic Chemical Feeders" Chlorinators (Slow Dissolve Tri-Chlor Only) and Brominators, Hayward Pool Products Inc. Website, <http://www.haywardnet.com/products/catalog/displayProdInfo.cfm?itemID=61>, 2 pages.
Hayward America's #1 Pool Water Systems Product Catalog, "Automatic Chemical Feeders" Chlorinators (Slow Dissolve Tri-Chlor Only) and Brominators, Buyers Guide, Hayward Pool Products Inc., Website, <http://www.haywardnet.com/products/catalog/displayProdInfo.cfm?itemID=60>, 2 pg.
Hayward Pool Products Owner's Guide, Installation and Operating Instructions, "Hayward Chemical Feeder", Models C250CF, C500CF, C1100CF, C1800CF, C2400CF,—1998—4 pages.
Krycer et al., "An Evaluation of Tablet Binding Agents Part II. Pressure Binders", Powder Technology, 1983, vol. 34, pp. 53-56.
March, "Advanced Organic Chem.", 1992, $4^{th}$ Edition, pp. 639-640.
Petterson, "N-Halogen Compounds. I. Decomposition of 1,3-Dichloro-5,5-dimethylhydantoin in Water at pH 9", J. Org. Chem., 1959, vol. 24, pp. 1414-1419.
Pentair Pool Products Brochure, "Rainbow High Capacity Chlorine/Bromine Feeders", "Unsurpassed Performance From The Industry's Leader in Automatic Sanitizing of Large Residential and Commercial Pools", date unknown, 1 page.
Pentair Pool Products Brochure, "Rainbow Model 300 Automatic Chlorine/Bromine Off-line Feeders", "The Efficient, Easy Way to Sanitize Your Pool or Spa", date unknown, 1 page.
Pentair Pool Products Brochure, "Rainbow Model 320 Automatic Chlorine/Bromine In-line Feeder", "Saves Time, Reduces Manual Handling of Chemicals", date unknown, 7 pages.
Sani-King Spa Feeder Product Brochure Model 740 from King Technology Website, <http://www.kingtechnology.com/spafeeder.htm> Visited (Aug. 10, 2001), 2000, 4 pages.
Sani-King Perform-Max Pool Sanitizer Instruction Guide, Models 910, 940, & 980 (Inline) and Models 930 & 960 (Off-line), date unknown, 16 pages.
Sani-King Adjust-A-Flo Product Brochure from King Technology Website <http://www.kingtechnology.com/spafeeder.htm> (Visited Aug. 10, 2001), 2000, 1 page.
Sani-King Perform-Max Sanitizers for Inground Pools Product Brochure for Model 940 & 960 from King Technology Website, <http://www.kingtechnology.com/perfermaxIG.htm>, visited Aug. 10, 2001, 2000, 1 pg.
Sani-King Perform-Max Sanitizers for Above Ground Pools Product Brochure Model 910 & 930 from King Technology Website, <http://www.kingtechnology.com/perfermaxIG.htm>, visited Aug. 10, 2001, 2000, 1 pg.
Fan et al., Huaxue Shijie (1998), 39(6), 297-300.
Perry's Chemical Engineers' Handbook (McGraw-Hill, 1999), Chapter 18, pp. 50/51.
Precipitation—Basic principles and industrial applications (Butterworth Heinemann, 1992), pp. 270 to 273.

PROCESS FOR PRODUCING N-HALOGENATED HYDANTOINS

REFERENCE TO RELATED APPLICATIONS

This is a Continuation-in-Part of commonly-owned prior application Ser. No. 10/919,097, filed Aug. 16, 2004, now abandoned, which is in turn a Continuation-in-Part of commonly-owned prior application Ser. No. 09/484,844, filed Jan. 18, 2000, now U.S. Pat. No. 6,809,205, all disclosure of which is incorporated herein by reference.

REFERENCE TO OTHER APPLICATIONS

Commonly-owned application Ser. No. 09/484,687, filed Jan. 18, 2000, now U.S. Pat. No. 6,508,954, by me and some of my colleagues, describes and claims 1,3-dibromo-5,5-dimethylhydantoin particulate solids producible by the processes of this application, such solids having unprecedented enhanced properties, and compacted articles made from such particulate solids without use of a binder. Commonly-owned application Ser. No. 09/487,816, filed Jan. 18, 2000, now U.S. Pat. No. 6,680,070, by some of my colleagues, relates in part to converting 1,3-dihalo-5,5-dimethylhydantoins into compacted articles using novel binders. Commonly-owned copending application Ser. No. 09/484,938, filed Jan. 18, 2000, now U.S. Pat. No. 6,565,868, by some of my colleagues, describes and claims methods for effecting efficacious microbiological control utilizing 1,3-dibromo-5,5-dimethylhydantoin in novel compacted or non-compacted forms. Commonly-owned application Ser. No. 09/484,891, filed Jan. 18, 2000, now U.S. Pat. No. 6,495,698, by one of my colleagues relates to the compacting of 1,3-dihalo-5,5-dimethylhydantoins other than 1,3-dibromo-5,5-dimethylhydantoin without use of binders, and to the novel compacted forms so produced. Commonly-owned application Ser. No. 09/483,896, filed Jan. 18, 2000, now U.S. Pat. No. 6,448,410, by some of my colleagues relates to the granulation of small average particle size 1,3-dibromo-5,5-dimethylhydantoin and also to the compaction of such granulated products to form larger-sized articles.

TECHNICAL FIELD

This invention relates to novel, highly efficient processes for the preparation of 1,3-dihalo-5-alkylhydantoins and 1,3-dihalo-5,5-dialkylhydantoins. As used herein, such terms as halogen, halogenated, and halo refer to bromine and/or chlorine.

BACKGROUND 1,3-Dihalo-5,5-dialkylhydantoins, especially 1,3-dibromo-5,5-dimethylhydantoin, 1,3-dichloro-5,5-dimethylhydantoin, 1-bromo-3-chloro-5,5-dimethylhydantoin, and 1-chloro-3-bromo-5,5-dimethylhydantoin, or mixtures of two or more of them, are biocidal agents for use in water treatment. These compounds are, in general, sparingly soluble in water.

Over the years considerable effort has been devoted to the search for improved methods for producing N-halogenated hydantoins. In U.S. Pat. No. 2,971,960 N-brominated compounds such as N-brominated 5,5-di-lower-alkyl hydantoins are formed by treating the alkylhydantoin with bromine in an acidic aqueous solution containing hypochlorite, preferably at a pH between 1 and 4. However, the method of choice has been halogenation of the alkylhydantoin in a basic aqueous medium. Almost invariably the halogen has been introduced into, or formed in situ in, the aqueous medium containing the alkylhydantoin. See in this connection U.S. Pat. Nos. 2,398,598; 2,779,764; 2,868,787; 2,920,997; 2,971,959; 3,121,715; 3,147,259; 4,532,330; 4,560,766; 4,654,424; 4,677,130; 4,745,189; WO 97/43264, published 20 Nov. 1997; Orazi and Meseri, *Anales Assoc. Quim. Argentina*, 1949, 37, 192-196; Orazi and Meseri, *Anales Assoc. Quim. Argentina*, 1950, 38, 5-11; Corral and Orazi, *J. Org. Chem.*, 1963, 23, 1100-1104; Jolles, *Bromine and its Compounds*, Ernest Benn, London, 1966, p. 365; and Markish and Arrad, *Ind. Eng. Chem. Res.*, 1995, 34, 2125-2127.

Shortcomings of prior processes for the N-halogenation of hydantoins include the requirement for careful temperature control (particularly in order to avoid sudden exotherms), long reaction times, foaming due to evolution of gases from decomposition of reactants and/or reaction products, and products of inconsistent quality.

It would be of considerable advantage if a new way could be found of producing N-halogenated hydantoins while avoiding or at least minimizing the extent of the shortcomings referred to above.

Another advantage would be the provision of process technology which enables production in a single halogenation step or operation of "tailor-made" mixtures of 1,3-dihalo-5,5-dialkylhydantoins (preferably 1,3-dihalo-5,5-dimethylhydantoins) even if such mixtures are not always of larger average particle size. By "tailor-made" mixtures is meant that through control or regulation of the halogenation process, it is possible to produce a reaction product containing a mixture of 1,3-dibromo-5,5-dialkylhydantoin together with N,N'-bromochloro-5,5-dialkylhydantoin(s) and optionally 1,3-dichloro-5,5-dialkylhydantoin in which proportions of these halogenated products in the mixture can be controlled so as to be within predetermined experimental limits. Some of these mixtures are new, and are useful as cost-effective biocides especially for water treatment applications.

This invention is deemed to fulfill these objectives in a most effective and efficient manner.

SUMMARY OF INVENTION

This invention provides processes for producing mixtures of halogenated hydantoins in a single halogenation step or operation. As used herein, the term "mixtures of halogenated hydantoins" refers to mixtures of 1,3-dihalohydantoins, more particularly, 1,3-dihalo-5-hydrocarbyl hydantoins and 1,3-dihalo-5,5-dihydrocarbyl hydantoins. At least some of these mixtures are new compositions of matter, which are useful as cost-effective biocides especially for water treatment applications. An advantage of this invention is that the parameters of the processes of the invention can be adjusted so that the mixtures produced are enriched in the 1,3-dibromohydantoin or the N,N'-bromochlorohydantoin. Another feature of this invention is that the average particle size of the product can be adjusted by adjusting the pH during the process. The halogenated hydantoins produced by the processes of this invention have good color characteristics (i.e., products are often white or off-white). In addition to the foregoing advantages, the processes of the invention are economical because the pH during the process, as well as the distribution of halogenated hydantoins produced, can be adjusted by varying the rates of feeding of the reagents for the processes. In other words, no additional component needs to be added to alter the pH or to enrich the product in a particular halogenated hydantoin.

In accordance with this invention processes are provided which are characterized by high efficiency, uniform product consistency, good product color, and efficient utilization of reactants. In addition, this invention makes possible the conduct of exothermic N-halogenation reactions without use of costly refrigeration. Moreover, the processes of this invention can be run in a batch mode, in a semi-batch mode, or in a continuous mode, and in any such mode it is possible, when producing products devoid of chromophoric groups, to obtain high yields of very pale yellow to almost pure white products. And no haloorganic solvent or co-solvent of any kind is required in the processes of this invention.

An embodiment of this invention is a process for the N-halogenation of at least one 5-hydrocarbyl hydantoin and/or at least one 5,5-dihydrocarbyl hydantoin. The process comprises concurrently feeding into a reaction zone (i) water, inorganic base, and 5,5-dimethylhydantoin, these being fed separately and/or in any combination(s), (ii) a separate feed of a brominating agent, and (iii) a separate feed of a chlorinating agent, in proportions such that during all or substantially all of the time the concurrent feeding is occurring halogenation of the 5-hydrocarbyl hydantoin and/or 5,5-dihydrocarbyl hydantoin occurs and resultant halogenated product precipitates in the liquid phase of an aqueous reaction mixture, and in which the pH of the liquid phase is continuously or substantially continuously maintained in the range of about 2.0 to about 8.0 during all or substantially all of the time the concurrent feeding is occurring.

Another embodiment of this invention is a process for the N-halogenation of at least one 5-hydrocarbyl hydantoin and/or at least one 5,5-dihydrocarbyl hydantoin. The process comprises:

A-1) concurrently or substantially concurrently feeding into in a reaction zone maintained at one or more temperatures in the range of about 20 to about 80° C., separate feeds of (i) an aqueous solution or slurry formed from an inorganic base and at least one 5-hydrocarbyl hydantoin and/or at least one 5,5-dihydrocarbyl hydantoin, (ii) a brominating agent, and (iii) a chlorinating agent; or A-2) concurrently or substantially concurrently feeding into a reaction zone maintained at one or more temperatures in the range of about 20 to about 80° C., at least four separate feeds, one of which is a brominating agent, another of which is a chlorinating agent, and at least two other feeds, at least one of which is selected from (a) and (b); and at least one of which is selected from (c) and (d), wherein (a) is an aqueous solution or slurry formed from an inorganic base,
(b) is an aqueous solution or slurry formed from an inorganic base and at least one 5-hydrocarbyl hydantoin and/or at least one 5,5-dihydrocarbyl hydantoin,
(c) at least one 5-hydrocarbyl hydantoin and/or at least one 5,5-dihydrocarbyl hydantoin, and
(d) is an aqueous solution or slurry formed from at least one 5-hydrocarbyl hydantoin and/or at least one 5,5-dihydrocarbyl hydantoin;

wherein the concurrent or substantially concurrent feeds in A-1 or in A-2 are in proportions such that 5-hydrocarbyl hydantoin and/or 5,5-dihydrocarbyl hydantoin is halogenated on both nitrogen atoms by bromine and/or chlorine atoms, and product is formed which precipitates in the aqueous reaction mixture continuously or substantially continuously during all or substantially all of the time the concurrent feeding is occurring; and B) preadjusting and/or adjusting or controlling (1) the ratio between the brominating agent and the chlorinating agent fed and (2) the amount of inorganic base fed such that the pH of the mixture in the reaction zone is continuously or substantially continuously maintained at a selected pH in the range of about 2.0 to about 5.5 during the time the concurrent or substantially concurrent feeding is occurring.

Still another embodiment of this invention is a composition of matter which comprises a halogenated 5-hydrocarbyl hydantoin or a halogenated 5,5-dihydrocarbyl hydantoin, which is a mixture of the 1,3-dibromo-, 1,3-dichloro-, and/or N,N'-bromochloro-species of the halogenated hydantoin.

These and other embodiments and features of this invention will be still further apparent from the ensuing description and appended claims.

FURTHER DETAILED DESCRIPTION OF THE INVENTION

As used throughout this document, the term "halogenating agent" is used to refer collectively to a brominating agent and a chlorinating agent.

The reactants used in the practice of this invention are comprised of the 5-hydrocarbyl and the 5,5-dihydrocarbyl hydantoins, with the 5,5-dihydrocarbyl hydantoins being preferred. Particularly preferred hydantoins are the 5-alkyl and 5,5-dialkyl hydantoins, especially those in which each alkyl group contains up to about 6 carbon atoms. Still more preferred are 5,5-dialkyl hydantoins in which each alkyl group contains, independently, up to 3 carbon atoms. Especially preferred is 5,5-dimethylhydantoin.

A wide variety of inorganic bases are suitable for use in the process of this invention. Typically these are water-soluble basic salts or oxides of an alkali metal or an alkaline earth metal. Preferred bases include sodium oxide, sodium hydroxide, sodium carbonate, sodium bicarbonate, potassium oxide, potassium hydroxide, potassium carbonate, potassium bicarbonate, calcium oxide, calcium hydroxide, or a mixture of any two or more of them.

In order to achieve the best results, the amount of base used is the stoichiometric quantity, or is substantially the stoichiometric quantity, theoretically required to deprotonate both nitrogen atoms of the 5-hydrocarbyl hydantoin and/or 5,5-dihydrocarbyl hydantoin, i.e., both the halogenatable amido group and the halogenatable imido group are deprotonated.

When conducting the process embodiments of this invention, especially when using a 5,5-dialkylhydantoin, more particularly 5,5-dimethylhydantoin, the proportions of water, inorganic base, and 5-hydrocarbyl hydantoin and/or 5,5-dihydrocarbyl hydantoin being fed should be such that when using an inorganic base having a monovalent cation, there can be from about 0.5 to about 2.5 moles of 5-hydrocarbyl hydantoin and/or 5,5-dihydrocarbyl hydantoin and from about 1.0 to about 5.0 moles of the base, per liter of water being fed, and preferably from about 1.0 to about 1.5 moles of 5-hydrocarbyl hydantoin and/or 5,5-dihydrocarbyl hydantoin and from about 2.0 to about 3.0 moles of the base, per liter of water being fed. When using an inorganic base having a divalent cation, there can be from about 0.5 to about 2.5 moles of 5-hydrocarbyl hydantoin and/or 5,5-dihydrocarbyl hydantoin and from about 0.5 to about 2.5 moles of the base, per liter of water being fed, and preferably about 1.0 to about 1.5 moles of 5-hydrocarbyl hydantoin and/or 5,5-dihydrocarbyl hydantoin and from about 1.0 to about 1.5 moles of the base, per liter of water being fed.

The water, inorganic base, and the 5-hydrocarbyl hydantoin and/or 5,5-dihydrocarbyl hydantoin can be fed individually or in any combination or mixture. However, it is advantageous to feed the inorganic base as an aqueous solution either with or without the co-presence of the 5-hydrocarbyl hydantoin and/or 5,5-dihydrocarbyl hydantoin. In this way, the heat generation that occurs when dissolving a base in water takes place prior to the introduction of such solution of aqueous base into the reaction zone. Most preferably, an aqueous solution of the inorganic base is formed, and to this solution is added the 5-hydrocarbyl hydantoin and/or 5,5-dihydrocarbyl hydantoin. Such a procedure not only safeguards against excessive heat generation which might otherwise adversely affect the 5-hydrocarbyl hydantoin and/or 5,5-dihydrocarbyl hydantoin, but simplifies the feeding operation and control of the proportions being fed. For best results, it is desirable to employ feed solutions having in the range of about 0.5 to about 2.5 moles of the 5-hydrocarbyl hydantoin and/or 5,5-dihydrocarbyl hydantoin per liter of water. In forming such solutions, use of aqueous alkaline solutions in the range of about 0.5 to about 5.0 moles of base per liter of water is preferred.

In the practice of this invention, halogenation of the 5-hydrocarbyl hydantoin and/or 5,5-dihydrocarbyl hydantoin is accomplished by use of a brominating agent and a chlorinating agent. Thus use can be made of bromine, chlorine, bromine chloride, bromine and chlorine, a bromide salt and chlorine and/or a source of hypochlorite anion, or an organic brominating or organic chlorinating agent such as N-bromosuccinimide, N-chlorosuccinimide, or pyridinium tribromide, and the like. Of these halogenating agents, bromine, chlorine, bromine chloride, bromine and chlorine, a bromide salt and chlorine and/or a source of hypochlorite anion are preferred. Particularly preferred are bromine, chlorine, and mixtures of bromine and chlorine (which will include or consist of bromine chloride). Highly preferred are bromine and chlorine, especially when the bromine and chlorine are separate feeds. Without desiring to be bound by theoretical considerations, it is believed that the actual species which carry out the halogenation in the aqueous reaction mixture can include, for example, one or more of $Br_2$, $Cl_2$, $BrCl$, $OBr^{\ominus}$, $OCl^{\ominus}$, $Br_3^{\ominus}$, $BrCl_2^{\ominus}$, $Cl_3^{\ominus}$, $Cl^{\oplus}$, and $Br^{\oplus}$. Whatever the actual halogenating species may be, the important thing is to feed to the aqueous reaction mixture suitable brominating agent and chlorinating agent that result in N-halogenation of both nitrogen atoms of the 5-hydrocarbyl hydantoin and/or 5,5-dihydrocarbyl hydantoin being halogenated.

If bromine is to be generated in situ, this is best accomplished by reaction between a suitable oxidant, preferably chlorine, and a bromine source such as a water-soluble alkali or alkaline earth metal bromide.

Bromide and/or chloride ions are generated from the brominating agent and/or chlorinating agent, respectively, during the halogenation of the 5-hydrocarbyl hydantoin and/or 5,5-dihydrocarbyl hydantoin. The bromide and/or chloride ions can be regenerated in situ to form more brominating agent and/or chlorinating agent via reaction with a suitable oxidant. Preferred oxidants are the brominating agent and/or chlorinating agent used in this invention.

The proportions of brominating agent and chlorinating agent relative to the 5-hydrocarbyl hydantoin and/or 5,5-dihydrocarbyl hydantoin should be such that there are at least about 1.8 atoms of the halogen per halogenatable amido or imido nitrogen atom to be halogenated. Preferably, there are in the range of about 1.8 to about 3.5 atoms of the halogen per halogenatable amido or imido nitrogen atom to be halogenated. Thus in the case of 5-hydrocarbyl hydantoins and/or 5,5-dihydrocarbyl hydantoins such as 5,5-dimethylhydantoin the proportions concurrently being fed to the reaction zone are such that there are at least about 3.7 atoms of halogen per molecule of 5-hydrocarbyl hydantoin and/or 5,5-dihydrocarbylhydantoin. Preferred are in the range of about 3.7 to about 7.0 atoms of halogen per molecule of 5-hydrocarbyl hydantoin and/or 5,5-dihydrocarbyl hydantoin. As previously noted, under ideal conditions the number of atoms of halogen per amido or imido nitrogen atoms to be halogenated would be precisely that amount required to produce the desired product without any deviation whatsoever from the selected stoichiometry. The fact that the foregoing ranges vary from such an ideal ratio simply reflects the fact that under actual large scale plant operating conditions, one can operate at slightly below the ideal ratio or slightly above the ideal ratio without material adverse effect relative to the optimum results achievable under such conditions. To the extent possible, it is preferable to operate with a slight excess of the halogen relative to the 5-hydrocarbyl hydantoin and/or 5,5-dihydrocarbyl hydantoin in the reaction mixture (i.e., in the range of about 2.0 to about 2.1 atoms of halogen per halogenatable amido and imido nitrogen atom to be halogenated) rather than operating continuously in the range of about 2.0 to about 1.9. This ensures full halogenation to the extent desired without use of excessive halogen and consequent loss of raw materials.

In the process of this invention, mixtures of halogenated hydantoins are frequently obtained, in the sense that a mixture of differently-halogenated products, viz. at least two of 1,3-dibromo-, 1,3-dichloro-, and N,N'-bromochloro-, and often all three, are present in the product mixture. The halogenated species which is predominate in the product can be influenced by controlling the ratios of brominating agent and chlorinating agent, especially the brominating agent, relative to the 5-hydrocarbyl hydantoin and/or 5,5-dihydrocarbyl hydantoin during the process. In particular, by operating within a pH range of about 2.0 to about 5.5 and utilizing a mole ratio between the separate feeds of bromine or other brominating agent and of chlorine or other chlorinating agent within the range of about 1:1 to about 1:2.5, new product mixtures of halogenated 5-hydrocarbyl hydantoin and/or halogenated 5,5-dihydrocarbyl hydantoin enriched in the 1,3-dibromo-species can be formed. Similarly, when the mole ratio between the separate feeds of bromine or other brominating agent and of chlorine or other chlorinating agent within the range of about 1:2.5 to about 1:4, new product mixtures of halogenated 5-hydrocarbyl hydantoin and/or halogenated 5,5-dihydrocarbyl hydantoin enriched in the N,N'-bromochloro-species can be formed. These enriched product mixtures are highly advantageous in that they are highly cost-effective biocides, especially for water treatment applications.

Typically the aqueous reaction mixtures of this invention will be formed, in essence, from five types of components, viz., the 5-hydrocarbyl hydantoin and/or 5,5-dihydrocarbyl hydantoin, the brominating agent, the chlorinating agent, the inorganic base, and water. Although it is preferable to minimize the number of components in the aqueous reaction mixture, it is possible to include one or more additional components in such mixtures, provided of course that such other component(s) cause(s) no material deleterious effect on the reaction or precipitate formation. For example, while not ordinarily recommended, it is possible to include certain organic solvents, especially water-miscible organic solvents in the aqueous reaction mixture. Such organic solvent(s) should be in proportions that do not result in a disproportionately large amount of the desired N-halogenated hydantoin end product remaining in solution, unless of course the solvent is to be subsequently removed, for example, by distillation. At least one potentially beneficial use of an organic solvent involves periodically including one or more organic solvents in the feeds to the reaction zone of the process being operated in a continuous mode in order to dissolve or dislodge encrustations of precipitate that may have built up in the reaction zone. If an organic solvent is to be included in the aqueous reaction mixture, besides not unduly affecting the intended N-halogenation reaction adversely, in the usual situation the solvent should not consume bromine or chlorine. Also, the solvent should not react with the intended N-halogenation product, should not interfere with the in situ generation of bromine (if such is being used), and should not result in formation of an unworkable or overly pasty or sticky precipitate or, in general have any other material adverse effect upon the conduct or further conduct of the process. A few examples of organic solvents that may be considered for use are N,N-dimethylformamide, dimethylsulfoxide, one or more $C_{1-4}$ alkanols, tetrahydrofuran or other saturated ethers, or the like. Therefore, unless expressly stated otherwise, the term "aqueous reaction mixture" as used anywhere in this document, including the claims, does not exclude the presence of one or more organic solvents, provided no material adverse effect upon the reaction or precipitate formation or product characteristics is caused by the presence of such solvent(s) in the amount in which present relative to the total amount of the overall reaction mixture.

When bromine is the brominating agent and/or chlorine is the chlorinating agent, the bromine and/or chlorine should be fed subsurface to the aqueous phase in the reaction zone so as to ensure intimate contact with the 5-hydrocarbyl hydantoin and/or 5,5-dihydrocarbyl hydantoin being used. When using an alkali metal bromide or an alkaline earth metal bromide and chlorine to generate bromine in situ, the bromide salt can be fed as a separate feed, typically as a water solution, or it can be fed along with an aqueous solution or slurry formed from the water-soluble base and the 5-hydrocarbyl hydantoin and/or 5,5-dihydrocarbyl hydantoin. In any such case, the chlorine used therewith should be fed subsurface to the aqueous phase in the reaction zone.

Chlorine will typically be fed into the reaction mixture as a liquid, but can be fed in the vapor state, if desired. Bromine can be fed into the reaction mixture either as a gas or as a liquid. Preferably the bromine is fed in the vapor state subsurface to the liquid phase of the aqueous reaction mixture, and it is desirable to so feed the gaseous bromine in admixture with an inert gas such as nitrogen or argon.

Although it is desirable and preferred to feed diatomic halogens ($Cl_2$, $Br_2$, BrCl, or mixtures thereof, and where the $Cl_2$ itself is being used as the chlorinating agent and/or is being used in combination with a bromine source such as an alkali metal bromide and/or an alkaline earth bromide) subsurface to the liquid phase of the aqueous reaction mixture, other ways of accomplishing the feeding can be used. One other way is to feed vaporous diatomic halogen into a headspace of a reactor while spraying aqueous reaction mixture and/or spraying or misting water into intimate contact with such vapors within the reactor. Other ways of establishing intimate contact of the diatomic halogen with the remainder of the components from which the aqueous reaction mixtures is formed include feeding the halogen as a liquid and/or as a solution into the aqueous reaction mixture, and in such case the halogen can be fed above the surface of the aqueous reaction mixture, if desired. In short, this invention contemplates the feeding of the halogen in any conceivable way that accomplishes the objective of bringing the components into intimate contact with each other so that the intended N-halogenation reaction will occur. In all cases, agitation of the aqueous reaction mixture is advantageous.

When bromine and chlorine are used as the brominating agent and chlorinating agent, respectively, they can be fed as separate feeds; separate feeds of bromine and chlorine are preferred. Alternatively, bromine and chlorine can be premixed in any desired proportions whereby the mixture being fed will contain bromine chloride, and if mixed in molar proportions other than 1:1, will also contain the halogen used in excess. In lieu of chlorine, an alkali or alkaline earth metal hypochlorite can be used as the chlorine source. Typically the hypochlorite salt will be fed in the form of an aqueous solution or slurry. However, it is also possible to feed a solid hypochlorite salt such as calcium hypochlorite directly into the aqueous reaction mixture. When bromination is desired, the brominating agent feed can be an alkali metal bromide or an alkaline earth metal bromide, and a source of chlorine, such as chlorine or an aqueous solution or slurry of an alkali or alkaline earth metal hypochlorite, such as sodium hypochlorite solution, in amounts sufficient to generate bromine in situ. It is also possible to feed a solid hypochlorite salt such as calcium hypochlorite to the aqueous reaction mixture in order to generate the bromine in situ. Usually feeds of this type will result in formation of products containing both bromine and chlorine in the molecule. While in principle other sources of bromine or chlorine may be used, such as organic compounds containing loosely bound bromine or chlorine, the use of such organic halogenating agents is not preferred as their use can complicate product workup and recovery operations. Moreover, such organic halogenating agents tend to be more expensive than such sources as bromine or chlorine, or sodium bromide and chlorine.

When feeding the brominating agent and chlorinating agent into the reactor, best results are achieved when such halogen source is introduced directly into the body of liquid within the reactor, i.e., below the surface of the heel or mother liquor when starting up the reaction and below the surface of the aqueous reaction mixture once the reaction has commenced. This will minimize the possibility of some of the halogen remaining in the headspace in the reactor and thus not participating in the reaction. Also feeds subsurface to the liquid phase of the reactor contents avoid splattering which can occur when, for example, liquid bromine strikes the surface of an aqueous mixture.

In this connection, in one of the embodiments of this invention, the 5-hydrocarbyl hydantoin and/or the 5,5-dihydrocarbyl hydantoin, inorganic base, brominating agent and chlorinating agent, and water can be fed either individually and/or in any combination(s) including a combination of all such components. If all such components are fed in combination with each other, this can result in these components coming together outside of a typical reactor or reaction vessel. In practicing such feeding, the components can initially be brought into contact with each other in a mixing device in proximity to, but apart from, such reactor or reaction vessel. Suitable mixing devices include a static mixer, a conduit (preferably a conduit in which there is turbulent flow), or a jet mixer that produces a high velocity effluent stream. In all such cases, the mixing device itself in which all of the foregoing components first come into contact with each other is part of the reaction zone.

In a continuous operation, usually and preferably, the effluent from the mixing device in which all of the foregoing components are first brought together is fed into a larger volume reactor or reaction vessel containing a body of the aqueous reaction mixture. Since reaction will begin essentially as soon as the foregoing components come into contact with each other, reaction will usually commence in such mixing device and will continue in the aqueous reaction mixture in the reactor or reaction vessel, which of course is also part of the reaction zone. Thus, it is desirable to place the mixing device, when using a mixing device, in close proximity to the larger volume reactor or reaction vessel and to move the components rapidly into, through, and from the mixing device and into a larger volume of aqueous reaction mixture in the larger reactor or reaction vessel. In this way, the time between initial contact among all of the components and the time when the aqueous reaction mixture comes into contact with a larger volume of the aqueous reaction mixture is kept short enough so that the temperature of the reaction mixture at any stage of the operation does not exceed about 90° C., and preferably does not exceed about 70° C. If desired, the mixing device, if used, can be cooled by indirect heat exchange with a cooling or refrigerated fluid.

When using a conduit with turbulent flow therein as the mixing device, such conduit can itself constitute the entire reactor or reaction vessel in a continuous operation. In other words, the reactor or reaction vessel itself can be a tubular reactor of sufficient length and volume for the reaction and precipitate formation to occur therein.

Preferably, the reactants are concurrently fed into a reaction zone composed of at least one reactor in which all of the components—whether fed individually or in any subcombination(s)—all come together for the first time and in which the N-halogenation reaction is initiated and carried out.

Preferably the pH in the processes of the invention is maintained in the range of about 2.0 to about 8.0. It is particularly preferred to conduct the processes of the invention while maintaining the pH within the range of about 2.0 to about 5.5. The processes of this invention can also be conducted at a pH in the range of about 5.5 to about 8.0.

Preferably the concurrent feeds in the processes of this invention are continuous feeds. It is also preferable that the feeds are at least co-feeds—i.e., at least two feeds are utilized, namely (i) an aqueous solution or slurry formed from an inorganic base and a 5-hydrocarbyl hydantoin and/or a 5,5-dihydrocarbyl hydantoin, and (ii) a brominating agent and a chlorinating agent. However, it is highly preferable to conduct a tri-feed process, where the feeds are (i) an aqueous solution or slurry formed from an inorganic base and a 5-hydrocarbyl hydantoin and/or a 5,5-dihydrocarbyl hydantoin, (ii) a brominating agent, and (iii) a chlorinating agent. It is also within the scope of this invention to conduct other multi-feed processes. Indeed, it is possible to utilize, for example, both a co-feed and a tri-feed although such an operation offers no particular advantage. In all cases, the feeds are proportioned such that the nitrogen atoms in the hydantoin molecule are substituted by a bromine or chlorine atom. Product formation occurs almost immediately upon the reaction components coming in contact with each other, and if no solids-containing heel or solids-free mother liquor from a prior reaction is used, precipitation begins shortly thereafter. Once precipitation has commenced, product formation and precipitation occur continuously or substantially continuously during the concurrent feeds. When a solids-containing heel or solids-free mother liquor from a prior reaction is used, the precipitation begins almost immediately and continues to occur continuously or substantially continuously during the concurrent feeds. The feeds are proportioned such that the pH in the aqueous reaction mixture is maintained or substantially continuously maintained in the range of about 2.0 to about 8.0, and preferably in the range of about 2.0 to about 5.5. Another preferred pH range is in the range of about 5.5 to about 8.0. In conducting the process, the materials in the concurrent feeds should rapidly come into intimate contact with each other. Thus, it is preferred to introduce the separate, but concurrent feeds, in close or relatively close proximity to each other and to provide sufficient agitation to cause such rapid intimate contact and resultant interaction among the components being fed.

Another highly important feature of this invention is the maintenance of the correct pH in the aqueous reaction mixture throughout substantially the entire reaction period. Here again, it is possible for slight departures to occur in the pH, particularly at the outset of the reaction. Such departures are within the ambit of this invention provided of course that no material adverse effects are encountered as a result of such departures. As noted above, the processes of this invention are typically conducted at a pH within the range of about 2.0 to about 8.0, and preferably in the range of about 5.5 to about 8.0. However, for best results the pH is most preferably maintained within the range of about 2.0 to about 5.5.

A feature of the processes of the invention is ability to influence the average particle size of the product. The average particle size appears at least nominally to vary directly with pH. As the pH increases, the average particle size increases; as the pH decreases, the average particle size decreases. Thus, when larger average particle sizes are desired, operation towards the higher end of the pH range is recommended. Conversely, when a smaller average particle size is desired, operation at lower pH values is recommended.

To maintain the desired pH in the aqueous reaction mixture, the rates at which the feeds of the base, brominating agent, and chlorinating agent play an important role. In particular, the halogenating agents should be fed or generated in situ at a rate sufficient to maintain the pH at the desired level (e.g., between 2.0 and 8.0, or preferably between 5.5 and 8.0, or most preferably between 2.0 and 5.5). In other words, the feed of halogen or the generation of halogen in situ should not be such as to decrease the pH (increase the acidity) of the reaction mixture to a pH significantly below about 2.0 for any substantial period of time. Without wishing to be bound by theory, it is believed that the chlorinating agent in particular has a greater impact on the pH Likewise, the base, whether fed singly, as an aqueous solution of base, or in admixture with water and the 5-hydrocarbyl hydantoin and/or 5,5-dihydrocarbyl hydantoin, should be fed at a rate insufficient to increase the pH above the desired level (e.g., 8.0 or preferably 5.5). Thus, the feeds should be suitably coordinated so as to maintain the pH of the reaction mixture within the ranges specified herein.

When using bromine or generating bromine in situ and forming a product of white coloration such as a 1,3-dihalo-5,5-dimethylhydantoin, a convenient way of monitoring the rate of bromine addition or generation is to feed or generate the bromine at a rate such that the color of the reaction mixture is bright yellow to reddish yellow or orange, particularly when bromine is used in an amount nearly equivalent or greater than the amount of chlorinating agent. The appearance of a reaction mixture having a reddish coloration can indicate that an excessive amount of bromine is present. Other ways of monitoring the halogen present can be used if desired, such as by use of pH meters, chemical pH indicators, and/or the like. Also the halogen feed or generation can be monitored by combinations of any two or more suitable methods for determining pH, such as a combination of color observations as described earlier in this paragraph, and use of one or more pH meters, concurrently or sequentially, or in any other suitable manner. If a combination of two or more ways of measuring pH are used, and if by chance disparate pH measurements result, one should rely upon the method previously determined in actual practice to give the most accurate and reproducible results. Use of carefully calibrated commercially-available pH meters is currently believed to be one of the most reliable ways of determining pH, but it is not intended that the scope of this invention be limited to use of pH meters.

While on the subject of pH control, operations in which the pH drifts above about 8.5 for any significant length of time are not desirable because in general the solubility of the desired product in the aqueous reaction mixture tends to increase under such elevated pH conditions. In fine-tuning an operation utilizing a process of this invention, one should strive to provide throughout at least most of the reaction time, a very slight stoichiometric excess of the halogen source relative to the 5-hydrocarbyl hydantoin and/or 5,5-dihydrocarbyl hydantoin to ensure achievement of complete halogenation to the desired level. For example, in order to minimize under-halogenation, slightly more than the number of equivalents of halogen atoms to be introduced into the 5-hydrocarbyl hydantoin and/or 5,5-dihydrocarbyl hydantoin should be employed, and should be maintained in the reaction mixture during substantially the entire time the feeds are being carried out.

Still another feature of this invention is that the concurrent feeding of the components enables the maintenance within the reactor of an aqueous reaction mixture of sufficiently low concentration that the reaction can be conducted at elevated temperatures (e.g., 40 to about 90° C.) without material decomposition of most 5-hydrocarbyl hydantoins and/or 5,5-dihydrocarbyl hydantoins, or the N-halogenated products thereof, depending of course upon the thermal decomposition temperature of the particular hydantoin being utilized. In sharp contrast, heretofore it has been commonplace to cool the reactor to temperatures as low as about 5° C. in order to ameliorate the problem of decomposition due to presence of excessive base in the system to which the halogen is added. Pursuant to this invention, it is preferred when operating in a continuous mode to feed the components from which the aqueous reaction mixture is composed in amounts such that the ratio of (i) the volume of the aqueous reaction mixture in liters to (ii) the moles of 5-hydrocarbyl hydantoin and/or 5,5-dihydrocarbyl hydantoin being fed to the reaction mixture per minute is in the range of about 10 to about 100 liters per mole per minute, and preferably in the range of about 30 to about 60 liters per mole per minute. Similarly, when operating in a batch mode wherein the feeds are to at least one reactor, until the volume of the reaction mixture reaches 50 percent of the total volume of the reactor(s), the feeds to the reaction mixture are maintained such that the ratio of (i) the volume of the reaction mixture in liters to (ii) the moles of the N-halogenatable compound being fed to the reaction mixture per minute is in the range of about 10 to about 100 liters per mole per minute, and preferably in the range of about 20 to about 80 liters per mole per minute. Then, when the volume of the reaction mixture is 50 percent or more of the total volume of the reactor(s), the feeds to the reaction mixture are such that the ratio of (i) the volume of the reaction mixture in liters to (ii) the moles of the 5-hydrocarbyl hydantoin and/or 5,5-dihydrocarbyl hydantoin being fed to the reaction mixture per minute is in the range of about 30 to about 60 liters per mole per minute. By operating a continuous, semi-batch, or batch process using the foregoing ratios, the 5-hydrocarbyl hydantoin and/or 5,5-dihydrocarbyl hydantoin and the N-halogenated derivative(s) thereof are less susceptible to thermal decomposition from the heat of reaction.

The processes of this invention can be carried out in various ways, such as in a batch mode, in a semi-batch mode, or, preferably, in a continuous mode. When conducting a continuous operation, it is desirable to design the operation such that the average residence time falls within the range of about 15 to about 100 minutes, and preferably in the range of about 30 to about 60 minutes. As with all of the numerical ranges given herein, departures therefrom are permissible whenever deemed necessary or desirable, provided only that such departures do not materially detract from the efficacy and effectiveness of the process.

In conducting the processes of this invention, the reaction temperatures can be varied within a reasonable range. Typically, the reaction temperature will fall within the range of about 10 to about 90° C. although under some conditions departures from this temperature range may prove acceptable under particular circumstances. Of ten times temperatures in the range of about 20 to about 80° C. or 90° C. will be found more efficacious. However, temperatures within the range of about 30 to about 70° C. are generally preferred inasmuch as reactions performed at these temperatures tend to produce products in the highest yields. It is most preferred to perform the reaction at temperatures in the range of about 40 to about 60° C., especially when utilizing a hydantoin such as 5,5-dimethylhydantoin, and bromine as the brominating agent. Temperatures in the range of about 40 to about 60° C. are most preferred because operations conducted within this range produce product in high yield at fast reaction rates and in the most cost-effective manner. When conducting the N-halogenation reaction at temperatures above the boiling temperature of the halogen being fed, it is desirable to feed the halogen subsurface to the liquid phase of the aqueous reaction mixture. In such a case, it is particularly desirable to feed the halogen diluted with an inert gas.

Yet another feature of this invention is the fact that the processes can be conducted adiabatically without material reduction in reactor throughput. Thus even when the process is conducted without adding heat energy into the reaction mixture and without recourse to refrigeration, or use of a flowing liquid heat transfer agent, or other ways of cooling (except possibly for normal unassisted heat transfer through the reactor walls to the surrounding atmosphere), the heat buildup from the exothermic reaction can be readily controlled without materially reducing feed rates. Such control can be achieved by maintaining a dilute aqueous reaction mixture, e.g., by operating a continuous, semi-batch, or batch process using the ratios of volume of reaction mixture to moles of N-halogenatable compound being fed per minute as described hereinabove. Despite such dilution, the reaction and precipitate formation nonetheless can proceed rapidly under such adiabatic conditions.

Even though adiabatic operation is possible, when conducting the processes of this invention, especially in a continuous mode, it is preferred to utilize a flow of cooling water or other heat exchange liquid for indirect heat exchange with the reactor contents to ensure maintenance of steady-state temperature conditions in the reaction mixture. If desired, however, the processes of this invention can be conducted using refrigeration.

The processes of this invention can be conducted in any of a variety of modes of operation. For example, the processes can be carried out in a batch mode, in a semi-batch mode with constant overflow, in a semi-batch mode without overflow, or in a continuous mode. The engineering details concerning such modes of process operation are well known in the art, as witness, for example, *Perry's Chemical Engineer's Handbook*, 4th Edition, McGraw-Hill, copyright 1963.

Because of the short reaction and precipitation times which are features of processes of this invention, it is possible, indeed preferred, to conduct the processes in a semi-batch mode, and more preferably in a continuous mode. This in itself is a rarity, as the literature on halogenation of 5-hydrocarbyl and 5,5-dihydrocarbyl hydantoins is replete with teachings involving only batch operations. In the continuous mode, reactor size can be substantially reduced without a loss in product output.

When conducted in a batch mode or when initiating a semi-batch or continuous process, it is preferred, although not required, to initially charge to the empty reactor either a solids-containing heel of a reaction mixture from a prior reaction in which the product to be formed had been formed or a solids-free mother liquor from such a prior reaction. Such heel or mother liquor typically has a pH in the range of about 6 to about 7, and usually contains up to 2 wt % of the product and/or a precursor thereof. Then the concurrent, suitably-proportioned feeds are initiated, typically at room temperature, and precipitate formation commences almost immediately, and in any event within a few minutes. In a batch operation, the feeds are typically continued until the reactor has been, or until the reactors have been, filled to the desired level. Usually at this point, the feeds are terminated, and the halogenated product which has formed and precipitated is recovered, typically by filtration, centrifugation, or decantation. Since the reaction is exothermic and rapid, long ride periods at the end of the feeding are normally unnecessary.

Observations to date while conducting the processes of this invention indicate that the reaction and precipitate formation are extremely fast. When no solids-containing heel or solids-free mother liquor from a prior reaction is used, the slight delay in the commencement of precipitate formation at the beginning of the concurrent feeds is believed to be simply the time required for the aqueous reaction mixture to become suitably saturated with the product. When a solids-containing heel or solids-free mother liquor from a prior reaction is used, little or no delay occurs in the commencement of precipitate formation at the beginning of the concurrent feeds. Because the rapidity of the reaction, upon termination of the concurrent feeds, precipitation may continue to occur in the aqueous reaction mixture for only a very short period of time.

Another feature of this invention is that the co-product is a relatively pure aqueous saline solution, thus minimizing environmental and disposal problems. Moreover, when using bromine as the halogen and an alkali or alkaline earth metal salt or oxide as the base in the process, the resultant co-product is an aqueous solution of alkali or alkaline earth metal bromide from which bromine can be recovered by oxidation of bromide ion to elemental bromine, for example by treatment of the solution with chlorine.

It can be seen therefore, whether operating in a batch mode, a semi-batch mode, or in a continuous mode, the initiation of the reaction with the utilization of a heel or mother liquor enables the more rapid achievement of efficient, steady-state operation than if a heel or mother liquor is not employed.

In a batch operation the aqueous reaction mixture is largely created and increased in volume by the feeds. In operations conducted in the batch, semi-batch, or continuous mode, it is highly desirable to vigorously agitate the reaction mixture to ensure thorough mixing of the reaction components.

The components of the reaction mixture should be agitated to a sufficient extent so as to avoid localized concentrations of either halogen or base. Thus, for example, in laboratory scale operations, stirring rates in the range of about 300-600 rpm have been found desirable for achieving good mixing within the reaction vessel. In plant scale operations use of a continuously stirred reactor is thus recommended.

In typical, properly conducted batch operations, during at least about 80% of the period of time the separate feeds are being fed concurrently, and preferably during at least about 90% of the foregoing period of time, precipitate is being formed that typically is essentially pure product (e.g., with a purity of at least about 80%, usually at least about 90%, and often as much as about 97% purity). Also, typically the desired product is formed in a yield of at least about 80%, and often as high as 94% or more, based on the amount of the 5-hydrocarbyl hydantoin and/or 5,5-dihydrocarbyl hydantoin used in the reaction. In typical, properly conducted continuous operations, once steady-state operation has been achieved, precipitate is continuously being formed that (a) also typically has a purity of at least about 96%, and often as much as 99.9%, and (b) typically is formed in a substantially continuous yield of at least about 85% based on the amount of the 5-hydrocarbyl hydantoin and/or 5,5-dihydrocarbyl hydantoin being fed as a reactant in the process.

If the reaction is performed in a reactor of sufficient size, the volume of the reactor contents can be cycled between predetermined low and high volumes with initiation of rapid draining when the volume reaches the high volume of reactor contents, and with discontinued draining once the volume reaches the low volume of reactor contents. However, it is preferred to conduct the process so that the volume of the contents of the reactor and the volume of the precipitate and portion of the reaction mixture removed from the reactor are equal or substantially equal whereby the volume of reactor contents remains constant or substantially constant. In this way, reactors with smaller volumes can be employed.

When operating in a continuous mode and once the continuous feeds have been initiated, the feeds may be adjusted in fine tuning the operation so as to establish and maintain the desired operating conditions for the steady-state operation. Such operation typically can be conducted without mishap for long periods of time before shutdown, e.g., for plant maintenance.

Thus, once steady-state conditions have been achieved in a continuous reactor, the separate feeds can be fed in appropriate proportions on a continuous basis, and the reactor contents maintained under the appropriate reaction conditions for virtually unlimited periods of time. Concurrently, a portion of the reaction mixture including precipitate (which mixture typically is in the form of a slurry) is being removed, usually and preferably continuously, from the reaction mixture so that the volume of the contents of the reactor remains more or less constant.

From the foregoing it can be seen that this invention involves an interrelationship among controllable reaction variables which result in the production of high quality products in high yield in rapid reactions. Thus, this invention features, inter alia, concurrent feeds of the reaction components with specified control of pH by means of feed rates. In preferred embodiments, adjustment and control of temperature enables rapid formation of product in high yield. Also, utilization of reaction mixtures in highly diluted conditions contributes materially, in preferred embodiments, to high yields and allows greater flexibility in operating temperatures. Moreover, the rapid precipitate formation under steady-state conditions makes possible the use of short residence times in continuous operations, and thus contributes materially to improved plant throughput.

It is to be noted that when the term "subsurface" is used anywhere in this document, including the claims, the term does not denote that there must be a headspace in the reaction zone. For example, if the reaction zone is completely filled with the aqueous reaction mixture (with equal rates of incoming and outgoing flows), the term "subsurface" means in this case that the substance being fed subsurface is being fed directly into the body of the aqueous reaction mixture, the surface thereof being defined by the enclosing walls of the reaction zone.

The use of the term "concurrent" does not exclude the possibility of inconsequential interruptions taking place during the feeds. Nor does this term imply that the feeds must start at exactly the same moment in time. In the case of a co-feed process, the two feeds can be initiated with an interval of time between such initiation as long as the interval is sufficiently short as to cause no material adverse effect upon the overall process. Likewise in the case of a tri-feed or multi-feed operation, there may be one or two different time intervals between or among the respective feeds, again provided that the time intervals are of sufficiently short duration to cause no material adverse effect upon the overall process.

The processes of this invention, whether performed in a batch mode, semi-batch mode, or continuous mode, are preferably conducted so that such things as the feeds, reaction, precipitate formation, and maintenance of specified pH occur "continuously" during the reaction. However, it cannot be stressed strongly enough that one must not gain the impression that inconsequential interruption in one or more of such things cannot occur. Interruptions which do not materially affect the conduct of the process are not excluded from the scope of this invention. To safeguard against hypertechnical legalistic word interpretation, it has been deemed prudent to employ terms such as "substantially continuously" in describing this invention. But whatever the terms used, the process should be conducted as one of ordinary skill in the art would carry out the processes after a thorough, unbiased reading of this entire disclosure and in keeping with the spirit of the invention gained from such a reading.

An important feature of this invention is the concurrent feeding of the separate feeds referred to above. It is again to be emphasized that the term "concurrent" does not imply that the feeds must start at exactly the same time or that they must stop at exactly the same period of time. Rather, the term is used in the sense that during substantially the entire reaction period, the designated feeds are being maintained. It should also be understood that while these concurrent feeds are preferably continuous concurrent feeds, slight interruptions in a feed are acceptable provided that the duration of the interruption is sufficiently small as to cause no material disruption in the reaction. Thus as used herein, the terms "concurrent" and "continuous" should be understood to embrace the minor departures just referred to. Naturally, those skilled in the art will strive to utilize the concurrent feeds with as little non-concurrence as possible. Likewise, those skilled in the art will of course seek to maintain the continuous feeds with as few interruptions as possible under the given circumstances in which the operation is being conducted. However, because the reaction mixtures are generally capable of standing for days without material change in composition, it is possible to interrupt an uncompleted operation (whether conducted in a batch mode, in a semi-batch mode, or in a continuous mode) for long periods of time should this become necessary.

The products of the processes of the invention are halogenated 5-hydrocarbyl hydantoins and halogenated 5,5-dihydrocarbyl hydantoins, and are obtained in high yield and purity from the reactor without need for further purification. As mentioned above, the average particle size of the products of the processes of this invention can be influenced by controlling the pH during the process. Typically, mixtures of halogenated hydantoins are obtained, in the sense of having a mixture of differently-halogenated products, viz. at least two of dibromo-, dichloro-, and bromochloro-, and frequently all three, being present in the product mixture. As noted above, which of the halogenated species (dibromo-, dichloro-, or bromochloro-), is predominate in the product can be influenced by controlling the ratios of brominating agent and chlorinating agent, especially the brominating agent, relative to the 5-hydrocarbyl hydantoin and/or 5,5-dihydrocarbyl hydantoin.

The compositions of the invention, which can be produced by the processes of this invention, are comprised of halogenated 5-hydrocarbyl hydantoins and halogenated 5,5-dihydrocarbyl hydantoins, and are normally a mixture of differently-halogenated products. The halogenated 5-hydrocarbyl hydantoins and halogenated 5,5-dihydrocarbyl hydantoins are 1,3-dibromo-, 1,3-dichloro-, and/or N,N'-bromochloro-derivatives of 5-hydrocarbyl hydantoins and 5,5-dihydrocarbyl hydantoins. Halogenated 5,5-dihydrocarbyl hydantoins are preferred. Particularly preferred halogenated hydantoins are halogenated 5-alkyl and halogenated 5,5-dialkyl hydantoins, especially those in which each alkyl group contains up to about 6 carbon atoms. Still more preferred are halogenated 5,5-dialkyl hydantoins in which each alkyl group contains, independently, up to 3 carbon atoms. Especially preferred are halogenated 5,5-dimethylhydantoins.

As just described for the products of this invention, the compositions of this invention are usually comprised of a mixture of differently-halogenated products. In preferred compositions, the dibromo- or the bromochloro-species is predominate. In compositions of the invention in which the bromochloro-species is predominate, it is preferred that the bromochloro-species is at least about 40% of the composition, while the dibromo-species is at least about 30% of the composition. Compositions of this invention in which the bromochloro-species is predominant preferably have an average particle size of at least about 50 microns, and more preferably at least about 75 microns. Particularly preferred compositions in which the bromochloro species is predominate are comprised of at least about 40% bromochloro-species and at least about 30% dibromo-species, and have an average particle size of at least about 50 microns. More preferably, the dibromo-species is predominate. Particularly preferred compositions of this invention in which the dibromo-species is predominate are those in which the dibromo-species comprises at least about 80% of the composition; especially preferred are such compositions in which the dibromo-species comprises at least about 90% of the composition. Compositions of this invention in which the dibromo-species is predominant preferably have an average particle size of at least about 50 microns, and more preferably at least about 100 microns. Highly preferred compositions are those in which the dibromo species comprises at least about 80% of the composition, and have an average particle size of at least about 50 microns, especially when the hydantoin is a halogenated 5,5-dimethylhydantoin.

As can be readily seen from the Examples hereinafter, this invention makes possible the provision of halogenated 5-hydrocarbyl hydantoins and halogenated 5,5-dihydrocarbyl hydantoins in high yield and purity. In fact, mixtures of halogenated hydantoins in which the dibromohydantoin is the predominate species have been obtained by use of the present process technology. Moreover, the 1,3-dihalo-5,5-dimethyl-hydantoins produced by processes of this invention are devoid of traces of organohalide solvent residues inasmuch as these products are formed in the absence of any halogenated organic solvent such as methylene chloride.

In the Examples, abbreviations for the hydantoins are used. DMH stands for 5,5-dimethylhydantoin; DBDMH stands for 1,3-dibromo-5,5-dimethylhydantoin; BCDMH stands for N,N'-bromochloro-5,5-dimethylhydantoin; and DCDMH stands for 1,3-dichloro-5,5-dimethylhydantoin. These abbreviations may also appear elsewhere in this document, and have the same meaning as just set forth.

The following Examples are presented to illustrate the practice of, and advantages made possible by, this invention. These Examples are not intended to limit, and should not be construed as limiting, the scope of this invention to the particular operations or conditions described therein. In Examples 1-7 liquid bromine (Aldrich) is fed subsurface into the reaction mixture. Both liquid bromine and the DMH/NaOH solutions are pumped into the reactor using Cole-Parmer Masterflex computerized drive (2 pump heads, 1 to 60 rpm) and Easy-Load pump head. For bromine, Viton tubing is used in connection with Teflon. For the DMH/NaOH solution, C-Flex tubing is used. Chlorine gas is bubbled into the reaction slurry, also subsurface. The NaOH solutions are made using regular tap water, then allowed to cool down to room temperature before adding the DMH to make a clear solution.

For the continuous run (Example 7), fractions (residence times) were collected manually such that the reactor level was maintained constant. Each fraction (typically 500 mL) was filtered and the original filtrate was analyzed within days. The solid was washed with tap water. Drying was carried out in filtration funnel under nitrogen or in vacuum oven at ~55° C. Co-feeding the reagents was monitored by use of a pH meter. The starting DMH (97%) was purchased from Aldrich. All reactions were carried out in a 4-neck 1-L jacketed glass flask. The reactor was equipped with a mechanical stirrer, a thermocouple, and a pH meter. The resulting reaction slurry was collected manually and intermittently from the bottom of the reactor. Each fraction was collected in a 500 mL flask.

The following analytical procedures were used in connection with Examples 1-7: DBDMH or BCDMH particle size was determined by use of Coulter LS particle size analyzer with typical run time of 1 minute per sample. The purity of the bromine content of both solid DBDMH and its filtrate was determined by iodometric titration. Proton NMR spectra were obtained in dry $CD_2Cl_2$ on a Bruker/GE Omega 400WB. The spectra were broadband C-13 decoupled to eliminate $^{13}C$ satellites. The residual proton resonance of the deuterated solvent was assigned to 5.32 ppm. Normalized wt % of the brominated and chlorinated species were calculated. The BCDMH was analyzed by $^1$H-NMR, in dried deuterated methylene chloride, to determine the isomers ratio. Each chemical shift represented the gem dimethyl group (6 H, s) in the hydantoin molecule.

Example 1

Batch Trifeed Operation at 53° C., pH~6-8

Into a 4-neck 1-L jacketed glass flask equipped with a mechanical stirrer (400 rpm), a thermocouple, and a pH meter and heated via a circulating bath, are charged a 200 mL heel of 5% NaCl solution. A solution of 5,5-dimethylhydantoin (DMH) is prepared by dissolving 44.5 g (1.11 mol) of NaOH in 339 g of water, and after cooling to room temperature, DMH (70.4 g, 0.549 mol) is added. The DMH solution is fed at 10.0 mL/min rate while the bromine is fed at ~0.80 mL/min subsurface. Chlorine is also co-fed subsurface in a rate such that the pH of the mixture ranges between 6 and 8. The reaction temperature is about 53° C. When the DMH feed ends, about 86.4 g of bromine is consumed (0.540 mol, ~98% of the bromine needed for total DMH bromination). The total amount of chlorine consumed is in the vicinity of about 0.8 mol. During the 44 minutes of the trifeed, a yellow to orange color persisted on the top of the reaction slurry. After filtering and washing the product with water, an off white solid (149.4 g, ~96% yield) was obtained. Filtrate analysis indicated the presence of ~0.2 wt. % of active bromine, ~0.3 wt % of bromide, and ~7.2% of chloride. Analytical data are summarized in Table 1. DBDMH was obtained in >98% purity with no dichloro species and only ~1 wt % of BCDMH.

Example 2

Batch Trifeed Operation 52° C., pH~5-7

The reagents are prepared as in Example 1 and the process is carried out similarly except that the pH of the slurry is kept between 5-7 (mostly between 5-6) by faster bubbling of the chlorine. About 87.7 g of bromine is consumed (0.548 mol, which is ~99% of the bromine needed for total DMH bromination) during the 38 minutes of the trifeed. Chlorine added during the trifeed is ~40.5 g (0.571 mol). The reaction slurry is mostly yellow, but at the end of addition a reddish color appears on the reaction surface and the slurry turns yellow when it reaches room temperature. After work up and drying, an off white solid (149.2 g, ~95%) is obtained. Analytical data are summarized in Table 1. DBDMH purity is ~92% with formation of 7 wt % of BCDMH and a trace of the 1,3-dichloro species.

Example 3

Batch Trifeed at 53° C., pH~5-6

The reagents were prepared as in Example 1 and the reaction was carried out similarly except that the pH of the slurry was maintained between 5-6 (mostly between 5-5.5) by faster bubbling of the chlorine. About 87.7 g bromine was consumed (0.548 mol, ~99% of the bromine needed for total DMH bromination) during the 38 minutes of the trifeed. Chlorine added during the trifeed was ~39 g (0.549 mol). A red orange color persisted on the surface of the reaction slurry. At the end of addition, the reaction filtrate was totally colorless. After work up and drying, an off white solid (149.8 g, ~96% yield) was obtained. Filtrate analysis indicated the presence of 0.2 wt % active bromine, ~0.6 bromide, and ~6.9% chloride. Analytical data are summarized in Table 1. DBDMH was obtained in 98% purity with no dichloro species, and only 1.7 wt % of BCDMH was present.

Example 4

Batch Trifeed at 44° C., pH~2-5

The reagents were prepared as in Example 1 and the reaction was carried out similarly except that the temperature was maintained at 44° C. and the pH of the slurry was maintained between 1.7-5.5 by faster bubbling of the chlorine. About 84.2 g bromine was consumed (0.527 mol, ~96% of the bromine needed for total DMH bromination) during the 41 minutes of the trifeed. Chlorine added during the trifeed was 74.2 g (1.046 mol). During the trifeed, an orange-yellow color persisted and a reddish color accumulated on the top of the slurry at the end of the additions. After work up and drying, a white powder (142.7 g, ~92% yield) was obtained. Analytical data are summarized in Table 1. DBDMH was obtained in ~82% purity with formation of 16 wt % of BCDMH and only ~1% dichloro species.

TABLE 1

| Ex. No. | Temp. | pH | Br$_2$ added, g | Isolated g (yield %) | APS* | Isomer Distribution DB:BC:DC** |
|---|---|---|---|---|---|---|
| 1 | 53° C. | 6-8 | 86.4 | 149.4 (>96) | 251.7 | 98.6:01.2:0.0 |
| 2 | 53° C. | 5-7 | 87.7 | 149.2 (>95) | 124.0 | 92.2:07.4:0.1 |
| 3 | 53° C. | 5-6 | 87.7 | 149.8 (>96) | 98.4 | 98.0:01.7:0.0 |
| 4 | 44° C. | 2-5 | 84.3 | 142.7 (~92) | 10.5 | 82.1:16.4:1.0 |

*APS refers to average particle size in microns.
**DB:BC:DC refers to DBDMH:BCDMH:DCDMH

Example 5

Batch Trifeed Operation at 53° C., pH 6-7

Into a heated 4-neck 1-L jacketed glass flask equipped with a mechanical stirrer (400-475 rpm), a thermocouple, and a pH meter was charged 200 mL heel of 5% NaCl solution. DMH solution was prepared by dissolving 44.5 g (1.11 mol) NaOH in 339 g water, and after cooling to room temperature DMH (70.4 g, 0.549 mol) was added producing ~400 mL homogeneous solution, ~1.37 M (Note that here the final halogenated DMH concentration is ~0.9 M since a heel of ~200 mL was used. This may in part explain the darker color of later residence times of continuous Example 7 below, while the color of the initial residence times are noticeably whiter). The DMH solution was fed at 10.0 mL/min rate while the bromine was fed at ~0.40 mL/min subsurface. Chlorine was bubbled subsurface at a rate such that the pH of the reaction mixture ranged between 6 and 7 and the reaction temperature was stabilized around 53° C. When the DMH feed ended, about 43.7 g bromine was consumed (0.273 mol) along with 66.6 g chlorine (~0.939 mol, i.e. added chlorine to bromine 3.4:1 or ~13% excess chlorine is used). During the 37 minutes of the trifeed, a lemon yellow color atop the slurry persisted and no reddish color accumulated on the top of the slurry as was observed in Examples 1-4. After slurry filtration (36° C.), washing with water (500 mL), and drying under nitrogen overnight, a very white solid (YI 6.75) was obtained (118.3 g, ~90% yield). Upon standing overnight, the colorless filtrate was found to contain few floating crystals indicating that filtration should be carried out at or below room temperature. Isomer distribution of the isolated BCDMH and other analytical data are summarized in Tables 2 and 3. The isomers distribution is similar to commercial samples.

Example 6

Batch Trifeed Operation at 53° C., pH~7

The reagents were prepared as in Example 5. Reaction was carried out similarly except the bromine feed rate was reduced by ~12% to 0.35 mL/min rate in an attempt to influence the isomers distribution while conducting the reaction at a pH around 7.0 by modifying the chlorine bubbling rate. About 42.5 g bromine was consumed (0.266 mol) and 53.5 g chlorine (~0.75 mol, i.e. added chlorine to bromine 2.8:1 or ~93% of the required chlorine) were added.

During the 41 minutes of the trifeed, the reaction slurry was almost colorless with no apparent halogen coloration. After slurry filtration (30° C.), washing with water (700 mL), and drying under nitrogen overnight, a white solid (YI 7.60) was obtained (105.1 g, ~80% yield). Isomers distribution of the isolated BCDMH and other analytical data are summarized in Tables 2 and 3. Higher than expected DBDMH ratio was obtained, apparently as a result of operating above pH 6.0 and addition of less than required stoichiometric chlorine.

In Table 2, the following abbreviations are used:
BC refers to N,N'-bromochloro-5,5-dimethylhydantoin;
DB refers to 1,3-dibromo-5,5-dimethylhydantoin;
DC refers to 1,3-dichloro-5,5-dimethylhydantoin;
MB refers to N- and/or N'-monobromo-5,5-dimethylhydantoin;
MC refers to N- and/or N'-monochloro-5,5-dimethylhydantoin;
YI refers to Yellowness Index;
APS refers to average particle size in microns.

TABLE 2

Isomers Distribution* and Properties

| Ex. No. | BC | DB | DC | MB | MC | YI | pH | APS | Yield % |
|---|---|---|---|---|---|---|---|---|---|
| 5 | 50.0 | 33.8 | 16.0 | 0.1 | nd | 6.7 | 6-7 | 101 | ~90 |
| 6 | 47.9 | 38.5 | 13.4 | 0.2 | 0.1 | 7.6 | 7 | 91 | ~80 |

*All ratios were determined by $^1$H-NMR in dry CD$_2$Cl$_2$, immediately after dissolving the solid.

TABLE 3

Wet Analysis of Trifeed Runs of Examples 5 and 6 as Related to Reactants

| | Assay | |
|---|---|---|
| | Example 5 | Example 6 |
| Wt % Active Bromine | 65.1 | 64.5 |
| Bromine | 36 | 38.7 |
| Chlorine | 13 | 11.3 |
| Nitrogen | 10.9 | 8.2 |
| pH at 5 minutes | 5.63 | 5.64 |
| pH at 10 minutes | 4.93 | 5.25 |
| pH at 15 minutes | 4.55 | 4.78 |
| Bromine Reacted, g | 43.7 | 42.5 |
| | (0.273 mol) | (0.266 mol) |
| Chlorine Used, g | 66.6 | 53.5 |
| | (0.94 mol) | (0.75 mol) |
| Product Collected, g | 118.3 | 105.1 |

The weight of added chlorine in Examples 5 and 6 was determined by calculating the weight difference before and after the trifeed process begins. From the results shown in Table 3 it was concluded that better chlorine control and continuous monitoring of chlorine weight would enable more precise achievement of a preselected ratio of intended products in the mixture formed in the reaction. Generally speaking, the total chlorine needed for approximately ~0.55 mol DMH=0.55 mol Cl$_2$ or 39.0 g in addition to enough chlorine to oxidize 0.266 mol of bromide or 18.9 g, i.e., a total of at least 57.9 g of chlorine.

Examples 1-6 above were conducted as batch operations. Example 7 hereinafter was conducted as a continuous process. Some of the main advantages of operating the continuous process are continuous removal of generated heat along with product in this exothermic bromination/in-situ oxidation/chlorination reaction. The benefit of co-feeding DMH/NaOH with the separate feeds of the halogens is the minimization of concentration buildup of any reagent at any given time. This allows a faster reaction rate at elevated temperatures and resulting product (e.g., BCDMH and DBDMH) precipitates out of solution almost immediately and steadily in a crystalline form. It becomes apparent that within the reactor that the reaction mixture is mostly product slurry and only very limited concentrations of halogens, DMH, or NaOH are present. Typically, only minimum amount of bromide is present and essentially no bromine. The rates of the feeds can be adjusted so that approximately stoichiometric amounts (i.e., theoretical amounts for producing BCDMH) are present (NaOH:DMH:Br$_2$:Cl$_2$=2.0:1.0:0.5:1.5) and all are present in small concentrations. As will be seen, the theoretical amounts for producing BCDMH actually resulted in production of a product enriched in both BCDMH and in DBDMH.

Example 7

Continuous Trifeed Operation at 53° C., pH~5.8-6.8

In this continuous tri-feed process, six fractions (i.e., continuous operation equivalent to six batch residence times) were collected manually at a rate such that the reactor level was constant. Fractions 1 and 2 were combined. Fractions 4 and 5 were also combined. Final reactor content was labeled as fraction # 6. Each fraction (500 mL) was filtered and the original filtrates were independently analyzed. The solids were washed with tap water. Drying was carried out in filtration funnel under nitrogen or in vacuum oven at ~60° C. Solids fractions obtained were also independently analyzed by iodometric titration, proton-NMR and for particle size measurements.

Into a 4-neck 1-L jacketed glass flask equipped with a mechanical stirrer (400 rpm mixing rate), a thermocouple, and a pH meter was charged 500 mL heel composed of 300 mL water and 200 mL filtrate of a previous batch run (either from Example 5 or 6). The reactor temperature was kept constant by using a circulating heating bath. DMH feed solution was prepared by dissolving 222.5 g of NaOH (5.56 mol) in 1690 g of water, and after cooling to room temperature the DMH (352 g, 2.74 mol) was added producing about two liters of a homogeneous solution, i.e., 1.37 M solution. (Note that the concentration of this run is similar to those of Examples 5 and 6. It is ~25% more concentrated, compared to DMH feed used in Examples 1 and 2, in which ~1.1 M DMH solution was co-fed with bromine, producing white DBDMH solid).

The DMH solution was fed at 10.0 mL/min rate while feeding liquid bromine at ~0.39 mL/min subsurface. Chlorine was bubbled also subsurface at a rate such that the pH or the reaction mixture ranged between 5.8 and 6.8 and the reaction temperature was stabilized around 53° C. When DMH feed ended, about 238.1 g of bromine (1.489 mol) was consumed (or 2.97 moles of bromonium ions, assuming all bromides are oxidized to bromine) and 276.5 g of chlorine (~3.89 mol, i.e., overall, added chlorine to bromine was 2.6:1 which means about 15% less chlorine is used due to the difficulty of maintaining precise gas control at the scale of operation being used. This also explains the greater DBDMH isomer distribution ratio that was achieved. The average residence time of each fraction was ~30 min. Each fraction was treated as a separate reaction mixture and was washed with an approximately equal volume water. After drying in a vacuum oven overnight, a total of 610 g of solid (~91% yield based on DMH and added bromine) was collected. Analyses of all the fractions (1-6) are summarized in Tables 4 and 5. Filtrates of fractions 3-6 were also examined by iodometric titration. The active halogen loss was minimal in the filtrates and indicates most of bromide was oxidized by chlorine, as can be seen in Table 6.

TABLE 4

Continuous Trifeed Process (With Fractions 1-6)

| Residence Time* | Isomer Distribution DB:BC:DC | Color (YI) | APS, microns |
|---|---|---|---|
| 1 + 2 | 40.9:44.7:14.2 | 7.05 | 72 |
| 3 | 44.1:44.4:11.4 | 8.55 | 120 |
| 4 + 5 | 39.6:46.3:13.8 | 8.86 | 174 |
| 6 | 34.8:47.1:17.8 | 7.93 | 73 |

*Each Residence time - or a combination of fractions - was treated as an independent reaction and separately analyzed.

TABLE 5

Analysis of Solid Fractions 1-6

| | Assay | | | |
|---|---|---|---|---|
| | 1 + 2 | 3 | 4 + 5 | 6 |
| Wt % Active Bromine | 64.7 | 63.9 | 64.7 | 65.6 |
| Bromine | 38.5 | 40.6 | 38.7 | 36.4 |
| Chlorine | 11.3 | 10.1 | 11.3 | 12.7 |
| Nitrogen | 10.8 | 10.7 | 10.7 | 11.1 |
| pH at 5 min. | 5.78 | 5.75 | 5.63 | 5.62 |
| pH at 10 min. | 5.40 | 5.43 | 5.28 | 5.18 |
| pH at 15 min. | 4.99 | 5.10 | 4.90 | 4.75 |

TABLE 6

Analysis of Continuous Trifeed Filtrates (of residence times 3-6)

| | Assay | | |
|---|---|---|---|
| | 3 | 4 + 5 | 6 |
| Wt % Active Bromine | 0.29 | 0.28 | 0.42 |
| Bromine | 0.2 | 0.2 | 0.2 |
| Chlorine | 8.7 | 8.6 | 7.0 |

The products of the above Examples which are product mixtures of halogenated 5,5-dimethylhydantoins enriched in the 1,3-dibromo-species or the N,N'-bromochloro-species constitute new, preferred highly cost-effective biocidal compositions of this invention.

It can be seen from the foregoing experimental results of the Examples that the new process technology of this invention makes possible control or regulation of the halogenation of a single 5-hydrocarbyl hydantoin or 5,5-dihydrocarbyl hydantoin (e.g., 5,5-dimethylhydantoin) to produce a reaction product containing a mixture of the 1,3-dibromohydantoin together with the N,N'-bromochlorohydantoin and optionally the 1,3-dichlorohydantoin in which proportions of these halogenated products in the mixture can be controlled so as to be within predetermined experimental limits. The process technology can also be applied to mixtures of 5-hydrocarbyl hydantoins and/or 5,5-dihydrocarbyl hydantoins as the starting material, and in this case more complicated mixtures of end products will be formed as the reaction product. Thus, for example, if using a mixture of two or more 5,5-dialkylhydantoins as the starting material, it is desirable to use a mixture of known composition.

Some exemplary embodiments of this invention are as follows:

A process for the N-halogenation of at least one 5-hydrocarbyl hydantoin and/or at least one 5,5-dihydrocarbyl hydantoin, which process comprises concurrently feeding into a reaction zone (i) water, inorganic base, and 5,5-dimethylhydantoin, these being fed separately and/or in any combination(s), (ii) a separate feed of a brominating agent, and (iii) a separate feed of a chlorinating agent, in proportions such that during all or substantially all of the time the concurrent feeding is occurring halogenation of both nitrogen atoms of said 5-hydrocarbyl hydantoin and/or 5,5-dihydrocarbyl hydantoin occurs and resultant halogenated product precipitates in the liquid phase of an aqueous reaction mixture, and in which the pH of said liquid phase is continuously or substantially continuously maintained in the range of about 2.0 to about 8.0 during all or substantially all of the time the concurrent feeding is occurring:

wherein the temperature of said aqueous reaction mixture is in the range of about 40 to about 60° C.; or wherein the proportions of water, inorganic base, and 5-hydrocarbyl hydantoin and/or 5,5-dihydrocarbyl hydantoin being fed are such that:
  A) where the inorganic base has a monovalent cation, there are from about 0.5 to about 2.5 moles of 5-hydrocarbyl hydantoin and/or 5,5-dihydrocarbyl hydantoin and from about 1.0 to about 5.0 moles of the base, per liter of water; and
  B) where the base has a divalent cation, there are about 0.5 to about 2.5 moles of 5-hydrocarbyl hydantoin and/or 5,5-dihydrocarbyl hydantoin and from about 0.5 to about 2.5 moles of the base, per liter of water; or wherein said pH is in the range of about 2.0 to about 5.5, and wherein the separate feeds of brominating agent and of chlorinating agent are proportioned such that a mole ratio of brominating agent to chlorinating agent is within the range of about 1:1 to about 1:2.5; or wherein said pH is in the range of about 2.0 to about 5.5, and wherein the separate feeds of brominating agent and of chlorinating agent are proportioned such that a mole ratio of brominating agent to chlorinating agent is within the range of about 1:2.5 to about 1:4.

A composition of matter which comprises a halogenated 5-hydrocarbyl hydantoin and/or a halogenated 5,5-dihydrocarbyl hydantoin, which is a mixture of the 1,3-dibromo-, 1,3-dichloro-, and/or N,N'-bromochloro-species of the halogenated hydantoin:
  wherein the N,N'-bromochloro-species is predominate, wherein the N,N'-bromochloro-species comprises at least about 40% of the composition, while the 1,3-dibromo-species comprises at least about 30% of the composition, and wherein the composition has an average particle size of at least about 75 microns; or
  wherein the 1,3-dibromo-species is predominate, and wherein the 1,3-dibromo-species comprises at least about 90% of the composition; or
  wherein the 1,3-dibromo-species is predominate, wherein the 1,3-dibromo-species comprises at least about 90% of the composition, and wherein the composition has an average particle size of at least about 50 microns; or
  wherein the 1,3-dibromo-species is predominate, wherein the 1,3-dibromo-species comprises at least about 80% of the composition, and wherein the composition has an average particle size of at least about 100 microns; or
  wherein the 1,3-dibromo-species is predominate, wherein the 1,3-dibromo-species comprises at least about 90% of the composition, and wherein the composition has an average particle size of at least about 100 microns.

As used in this document, the term "water-soluble" means that the substance being described has at least sufficient solubility in water to form an aqueous solution containing at least a sufficient amount of such dissolved substance (presumably in ionized form) to enable the operation in which such solution is being used, to be carried out under the particular conditions in which the solution is being employed. Naturally it is desirable that the substance have a greater solubility than this in water under such conditions. However, the term does not mean that the substance must dissolve in all proportions in water under such conditions.

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

It will also be understood that the terms "substantial" and "substantially" denote that chemical processes ordinarily do not involve absolutes. Thus instead of describing a variable as an absolute, it is far more realistic to describe the variable as being in the substantial vicinity of the expressed variable. For example when describing a stoichiometric quantity it is far more realistic to refer to the quantity as being substantially a stoichiometric quantity since one skilled in the art fully realizes that slight deviations from the absolute stoichiometry would produce no appreciable difference in results. Thus in any and all respects, this document should be read with the application of common sense.

Each and every patent or other publication or published document referred to in any portion of this specification is incorporated in toto into this disclosure by reference, as if fully set forth herein.

This invention is susceptible to considerable variation within the spirit and scope of the appended claims.

The invention claimed is:

1. A process for the N-halogenation of at least one 5-hydrocarbyl hydantoin and/or at least one 5,5-dihydrocarbyl hydantoin, which process comprises concurrently feeding into a reaction zone (i) water, inorganic base, and at least one 5-hydrocarbyl hydantoin and/or at least one 5,5-dihydrocarbyl hydantoin, these being fed separately and/or in any combination(s), (ii) a separate feed of a brominating agent, and (iii) a separate feed of a chlorinating agent, in proportions such that during all or substantially all of the time the concurrent feeding is occurring halogenation of both nitrogen atoms of said 5-hydrocarbyl hydantoin and/or 5,5-dihydrocarbyl hydantoin occurs and resultant halogenated product precipitates in the liquid phase of an aqueous reaction mixture, and in which the pH of said liquid phase is continuously or substantially continuously maintained in the range of about 2.0 to about 8.0 during all or substantially all of the time the concurrent feeding is occurring.

2. A process of claim 1 wherein said pH is in the range of about 2.0 to about 5.5.

3. A process of claim 1 wherein said pH is in the range of about 5.5 to about 8.0.

4. A process of claim 2 wherein said aqueous reaction mixture is at a temperature in the range of about 30 to about 70° C.

5. A process of claim 2 wherein (ii) is bromine and is fed subsurface to the liquid phase of said reaction mixture and wherein (iii) is chlorine and is fed subsurface to the liquid phase of said reaction mixture.

6. A process of claim 2 wherein said 5-hydrocarbyl hydantoin and/or 5,5-dihydrocarbyl hydantoin is a 5-alkyl hydantoin or a 5,5-dialkyl hydantoin, and wherein each alkyl group contains up to about 6 carbon atoms.

7. A process of claim 2 wherein the proportions of water, inorganic base, and 5-hydrocarbyl hydantoin and/or 5,5-dihydrocarbyl hydantoin being fed are such that:
  A) where the inorganic base has a monovalent cation, there are from about 1.0 to about 1.5 moles of 5-hydrocarbyl hydantoin and/or 5,5-dihydrocarbyl hydantoin and from about 2.0 to about 3.0 moles of the base, per liter of water; and
  B) where the base has a divalent cation, there are about 1.0 to about 1.5 moles of 5-hydrocarbyl hydantoin and/or 5,5-dihydrocarbyl hydantoin and from about 1.0 to about 1.5 moles of the base, per liter of water.

8. A process of claim 2 wherein (ii) is bromine; wherein said aqueous reaction mixture is at a temperature in the range of about 30 to about 70° C.; and wherein if said temperature is above the boiling point of the bromine, the bromine is fed subsurface to the liquid phase of said reaction mixture.

9. A process of claim 8 wherein said 5-hydrocarbyl hydantoin and/or 5,5-dihydrocarbyl hydantoin is a 5,5-dialkyl hydantoin, and wherein each alkyl group contains, independently, up to 3 carbon atoms.

10. A process of claim 8 wherein said base is sodium hydroxide, and wherein said aqueous reaction mixture is at a temperature in the range of about 40 to about 60° C.

11. A process of claim 10 wherein said 5-hydrocarbyl hydantoin and/or 5,5-dihydrocarbyl hydantoin is 5,5-dimethylhydantoin.

12. A process of claim 2 wherein the water, inorganic base, and 5-hydrocarbyl hydantoin and/or 5,5-dihydrocarbyl hydantoin of (i) are introduced as a feed solution formed from all three of them by mixing 5-hydrocarbyl hydantoin and/or 5,5-dihydrocarbyl hydantoin with an aqueous solution of inorganic base.

13. A process of claim 12 wherein the inorganic base used in forming said feed solution is a water-soluble basic salt or oxide of an alkali metal or an alkaline earth metal.

14. A process of claim 12 wherein the inorganic base used in forming said feed solution consists essentially of sodium oxide, sodium hydroxide, sodium carbonate, sodium bicarbonate, potassium oxide, potassium hydroxide, potassium carbonate, potassium bicarbonate, calcium oxide, calcium hydroxide, or a mixture of any two or more of them; and wherein the amount of such base is the stoichiometric quantity, or is substantially the stoichiometric quantity, theoretically required to fully deprotonate the 5-hydrocarbyl hydantoin and/or 5,5-dihydrocarbyl hydantoin used in forming said feed solution.

15. A process of claim 12 wherein the process is conducted in a batch mode by initiating the concurrent feeds of (i) and (ii) to the reactor containing (a) a solids-containing heel of a reaction mixture from a prior reaction in which the halogenated product to be formed had been formed, or (b) a solids-free mother liquor of a reaction mixture from a prior reaction in which the halogenated product to be formed had been formed, and discontinuing the concurrent feeds of (i) and (ii) when the reactor has been filled to the desired level; wherein said 5-hydrocarbyl hydantoin and/or 5,5-dihydrocarbyl hydantoin is a 5-alkyl hydantoin or a 5,5-dialkyl hydantoin, and wherein each alkyl group contains up to about 6 carbon atoms.

16. A process of claim 2 wherein the process is conducted in a batch mode by initiating the concurrent feeds of (i) and (ii) to a reactor containing (a) a solids-containing heel of a reaction mixture from a prior reaction in which the halogenated product to be formed had been formed, or (b) a solids-free mother liquor of a reaction mixture from a prior reaction in which the halogenated product to be formed had been formed, and discontinuing the concurrent feeds of (i) and (ii) when the reactor has been filled to the desired level.

17. A process of claim 2 wherein the separate feeds of brominating agent and of chlorinating agent are proportioned such that a mole ratio of brominating agent to chlorinating agent is within the range of about 1:1 to about 1:2.5.

18. A process of claim 2 wherein the separate feeds of brominating agent and of chlorinating agent are proportioned such that a mole ratio of brominating agent to chlorinating agent is within the range of about 1:2.5 to about 1:4.

19. A process of claim 3 wherein said aqueous reaction mixture is at a temperature in the range of about 30 to about 70° C.

20. A process of claim 3 wherein (ii) is bromine and is fed subsurface to the liquid phase of said reaction mixture and wherein (iii) is chlorine and is fed subsurface to the liquid phase of said reaction mixture.

21. A process of claim 3 wherein said 5-hydrocarbyl hydantoin and/or 5,5-dihydrocarbyl hydantoin is a 5-alkyl hydantoin or a 5,5-dialkyl hydantoin, and wherein each alkyl group contains up to about 6 carbon atoms.

22. A process of claim 3 wherein the proportions of water, inorganic base, and 5-hydrocarbyl hydantoin and/or 5,5-dihydrocarbyl hydantoin being fed are such that:
  A) where the inorganic base has a monovalent cation, there are from about 1.0 to about 1.5 moles of 5-hydrocarbyl hydantoin and/or 5,5-dihydrocarbyl hydantoin and from about 2.0 to about 3.0 moles of the base, per liter of water; and
  B) where the base has a divalent cation, there are about 1.0 to about 1.5 moles of 5-hydrocarbyl hydantoin and/or 5,5-dihydrocarbyl hydantoin and from about 1.0 to about 1.5 moles of the base, per liter of water.

23. A process of claim 3 wherein (ii) is bromine; wherein said aqueous reaction mixture is at a temperature in the range of about 30 to about 70° C.; and wherein if said temperature is above the boiling point of the bromine, the bromine is fed subsurface to the liquid phase of said reaction mixture.

24. A process of claim 23 wherein said 5-hydrocarbyl hydantoin and/or 5,5-dihydrocarbyl hydantoin is a 5,5-dialkyl hydantoin, and wherein each alkyl group contains, independently, up to 3 carbon atoms.

25. A process of claim 23 wherein said base is sodium hydroxide, and wherein the temperature of said aqueous reaction mixture is in the range of about 40 to about 60° C.

26. A process of claim 25 wherein said 5-hydrocarbyl hydantoin and/or 5,5-dihydrocarbyl hydantoin is 5,5-dimethylhydantoin.

27. A process of claim 3 wherein the water, inorganic base, and 5-hydrocarbyl hydantoin and/or 5,5-dihydrocarbyl hydantoin of (i) are introduced as a feed solution formed from all three of them by mixing 5-hydrocarbyl hydantoin and/or 5,5-dihydrocarbyl hydantoin with an aqueous solution of inorganic base.

28. A process of claim 27 wherein the inorganic base used in forming said feed solution is a water-soluble basic salt or oxide of an alkali metal or an alkaline earth metal.

29. A process of claim 27 wherein the inorganic base used in forming said feed solution consists essentially of sodium oxide, sodium hydroxide, sodium carbonate, sodium bicarbonate, potassium oxide, potassium hydroxide, potassium carbonate, potassium bicarbonate, calcium oxide, calcium hydroxide, or a mixture of any two or more of them; and wherein the amount of such base is the stoichiometric quantity, or is substantially the stoichiometric quantity, theoretically required to fully deprotonate the 5-hydrocarbyl hydantoin and/or 5,5-dihydrocarbyl hydantoin used in forming said feed solution.

30. A process of claim 27 wherein the process is conducted in a batch mode by initiating the concurrent feeds of (i) and (ii) to the reactor containing (a) a solids-containing heel of a reaction mixture from a prior reaction in which the halogenated product to be formed had been formed, or (b) a solids-free mother liquor of a reaction mixture from a prior reaction in which the halogenated product to be formed had been formed, and discontinuing the concurrent feeds of (i) and (ii) when the reactor has been filled to the desired level; wherein said 5-hydrocarbyl hydantoin and/or 5,5-dihydrocarbyl hydantoin is a 5-alkyl hydantoin or a 5,5-dialkyl hydantoin, and wherein each alkyl group contains up to about 6 carbon atoms.

31. A process of claim 3 wherein the process is conducted in a batch mode by initiating the concurrent feeds of (i) and (ii) to a reactor containing (a) a solids-containing heel of a reaction mixture from a prior reaction in which the halogenated product to be formed had been formed, or (b) a solids-free mother liquor of a reaction mixture from a prior reaction in which the halogenated product to be formed had been formed, and discontinuing the concurrent feeds of (i) and (ii) when the reactor has been filled to the desired level.

32. A process of claim 3 wherein the separate feeds of brominating agent and of chlorinating agent are proportioned such that a mole ratio of brominating agent to chlorinating agent is within the range of about 1:1 to about 1:2.5.

33. A process of claim 3 wherein the separate feeds of brominating agent and of chlorinating agent are proportioned such that a mole ratio of brominating agent to chlorinating agent is within the range of about 1:2.5 to about 1:4.

34. A process for the N-halogenation of at least one 5-hydrocarbyl hydantoin and/or at least one 5,5-dihydrocarbyl hydantoin, which process comprises:
A-1) concurrently or substantially concurrently feeding into in a reaction zone maintained at one or more temperatures in the range of about 20 to about 80° C., separate feeds of (i) an aqueous solution or slurry formed from an inorganic base and at least one 5-hydrocarbyl hydantoin and/or at least one 5,5-dihydrocarbyl hydantoin, (ii) a brominating agent, and (iii) a chlorinating agent; or
A-2) concurrently or substantially concurrently feeding into a reaction zone maintained at one or more temperatures in the range of about 20 to about 80° C., at least four separate feeds, one of which is a brominating agent, another of which is a chlorinating agent, and at least two other feeds, at least one of which is selected from (a) and (b); and at least one of which is selected from (c) and (d), wherein
  (a) is an aqueous solution or slurry formed from an inorganic base,
  (b) is an aqueous solution or slurry formed from an inorganic base and at least one 5-hydrocarbyl hydantoin and/or at least one 5,5-dihydrocarbyl hydantoin,
  (c) at least one 5-hydrocarbyl hydantoin and/or at least one 5,5-dihydrocarbyl hydantoin, and
  (d) is an aqueous solution or slurry formed from at least one 5-hydrocarbyl hydantoin and/or at least one 5,5-dihydrocarbyl hydantoin;
  wherein the concurrent or substantially concurrent feeds in A-1 or in A-2 are in proportions such that 5-hydrocarbyl hydantoin and/or 5,5-dihydrocarbyl hydantoin is halogenated on both nitrogen atoms by bromine and/or chlorine atoms, and product is formed which precipitates in the aqueous reaction mixture continuously or substantially continuously during all or substantially all of the time the concurrent feeding is occurring; and
B) preadjusting and/or adjusting or controlling (1) the ratio between the brominating agent and the chlorinating agent fed and (2) the amount of inorganic base fed such that the pH of the mixture in the reaction zone is continuously or substantially continuously maintained at a selected pH in the range of about 2.0 to about 5.5 during the time said concurrent or substantially concurrent feeding is occurring.

35. A process as in claim 34 wherein the concurrent feeding of A-1 is used.

36. A process as in claim 35 wherein the separate feed of (i) is an aqueous solution or slurry formed from an inorganic base and a single 5,5-dialkyl hydantoin, and wherein each alkyl group contains, independently, up to 3 carbon atoms.

37. A process as in claim 35 wherein the separate feed of (i) is an aqueous solution or slurry formed from an inorganic base and 5,5-dimethylhydantoin.

38. A process as in claim 35 wherein the separate feed of (ii) is bromine, and the separate feed of (iii) is chlorine.

39. A process as in claim 35 wherein the separate feed of (i) is an aqueous solution or slurry formed from an inorganic base and a single 5,5-dialkyl hydantoin, and wherein each alkyl group contains, independently, up to 3 carbon atoms, wherein the separate feed of (ii) is bromine, and wherein the separate feed of (iii) is chlorine.

40. A process as in claim 34 wherein the concurrent feeding of A-2 is used.

41. A process as in claim 40 wherein the brominating agent used is bromine and wherein the chlorinating agent used is chlorine.

42. A process as in claim 40 wherein the at least one 5-hydrocarbyl hydantoin and/or at least one 5,5-dihydrocarbyl hydantoin in each of (b), (c), and (d) is a single 5,5-dialkyl hydantoin, and wherein each alkyl group contains, independently, up to 3 carbon atoms.

43. A process as in claim 40 wherein the at least one 5-hydrocarbyl hydantoin and/or at least one 5,5-dihydrocarbyl hydantoin in each of (b), (c), and (d) is 5,5-dimethylhydantoin.

44. A process as in claim 40 wherein the brominating agent used is bromine, wherein the chlorinating agent used is chlorine, wherein the at least one 5-hydrocarbyl hydantoin and/or at least one 5,5-dihydrocarbyl hydantoin in each of (b), (c), and (d) is a single 5,5-dialkyl hydantoin, and wherein each alkyl group contains, independently, up to 3 carbon atoms.

45. A process as in claim 40 wherein the brominating agent used is bromine, wherein the chlorinating agent used is chlorine, and wherein the at least one 5-hydrocarbyl hydantoin and/or at least one 5,5-dihydrocarbyl hydantoin in each of (b), (c), and (d) is 5,5-dimethylhydantoin.

46. A process of claim 34 wherein the separate feeds of brominating agent and of chlorinating agent are proportioned such that a mole ratio of brominating agent to chlorinating agent is within the range of about 1:1 to about 1:2.5.

47. A process of claim 34 wherein the separate feeds of brominating agent and of chlorinating agent are proportioned such that a mole ratio of brominating agent to chlorinating agent is within the range of about 1:2.5 to about 1:4.

* * * * *